US010081801B2

(12) United States Patent
Mikkelsen et al.

(10) Patent No.: US 10,081,801 B2
(45) Date of Patent: Sep. 25, 2018

(54) MUTANT SIALIDASE HAVING TRANS-SIALIDASE ACTIVITY FOR USE IN PRODUCTION OF SIALYLATED GLYCANS

(71) Applicant: DANMARKS TEKNISKE UNIVERSITET, Kgs. Lyngby (DK)

(72) Inventors: Jørn Dalgaard Mikkelsen, Hvidovre (DK); Carsten Jers, Rødovre (DK); Malwina Michalak, Vejle (DK); Kasper Planeta Kepp, Copenhagen (DK); Dorte Møller Larsen, Frederiksberg (DK)

(73) Assignee: DANMARKS TEKNISKE UNIVERSITET, Kgs. Lyngby (DK)

( * ) Notice: Subject to any disclaimer, the term of this patent is extended or adjusted under 35 U.S.C. 154(b) by 185 days.

(21) Appl. No.: 14/783,967

(22) PCT Filed: Apr. 11, 2014

(86) PCT No.: PCT/EP2014/057422
§ 371 (c)(1),
(2) Date: Oct. 12, 2015

(87) PCT Pub. No.: WO2014/167112
PCT Pub. Date: Oct. 16, 2014

(65) Prior Publication Data
US 2016/0076013 A1 Mar. 17, 2016

(30) Foreign Application Priority Data
Apr. 12, 2013 (EP) ..................... 13163551

(51) Int. Cl.
C12N 9/24 (2006.01)
A61K 31/70 (2006.01)
A61K 31/7016 (2006.01)
A61K 31/702 (2006.01)
A23L 33/00 (2016.01)
A23L 33/10 (2016.01)

(52) U.S. Cl.
CPC ............ *C12N 9/2402* (2013.01); *A23L 33/10* (2016.08); *A23L 33/40* (2016.08); *A61K 31/702* (2013.01); *A61K 31/7016* (2013.01); *A23V 2002/00* (2013.01); *C12Y 302/01018* (2013.01); *Y02A 50/414* (2018.01); *Y02P 20/582* (2015.11)

(58) Field of Classification Search
None
See application file for complete search history.

(56) References Cited

FOREIGN PATENT DOCUMENTS

WO WO 99/08511 * 2/1999

OTHER PUBLICATIONS

Milk Facts—Retrived from < http://www.milkfacts.info/Milk%20Composition/Carbohydrate.htm > on Nov. 15, 2017.*
Amaya MF, Watts AG, Damager I, Wehenkel A, Nguyen T, et al. (2004) "Structural insights into the catalytic mechanism of Trypanosoma cruzi trans-sialidase." Structure 12: 775-784.
Bode, 2012, "Human milk oligosaccharides: Every baby needs a sugar mama," Glycobiology 22(9): 1147-1162.
Buschiazzo A, Amaya MF, Cremona ML, Frasch AC, Alzari PM (2002) "The crystal structure and mode of action of trans-sialidase, a key enzyme in Trypanosoma cruzi pathogenesis." Mol Cell 10: 757-768.
Buschiazzo A, Cremona, ML, Campetella O, Frasch ACC and Sánchez DO. (1993) "Sequence of a Ttypansoma rangeli gene closely related to Trypansoma cruzi trans-sialidase." Molecular and Biochemical Parasitology, 62 (1993) 115-116.
Buschiazzo A, Tavares GA, Campetella O, Spinelli S, Cremona ML, et al. (2000) "Structural basis of sialyltransferase activity in trypanosomal sialidases." EMBO J 19: 16-24.
Chen X, Varki A (2010) "Advances in the biology and chemistry of sialic acids." ACS Chem Biol 5: 163-176.
Damager I, Buchini S, Amaya MF, Buschiazzo A, Alzari P, et al. (2008) "Kinetic and mechanistic analysis of Trypanosoma cruzi trans-sialidase reveals a classical ping-pong mechanism with acid/base catalysis." Biochemistry 47: 3507-3512.
Denny PC, Denny PA, Allerton SE (1983) "Determination of sialic acid using 2-thiobaibituric acid in the absence of hazardous sodium arsenite." Clin Chian Acta 131: 333-336.
Eiwegger et al., "Human Milk-Derived Oligosaccharides and Plant-Derived Oligosaccharides Stimulate Cytokine Production of Cord Blood T-Cells In Vitro," 2004, Pediatric Rev. 56:536-540.
Gaskell A, Crennell S, Taylor G. (1995) "The three domains of a bacterial sialidase: a beta-propeller, an immunoglobulin module and a galactose-binding jelly-roll." Structure 3:1197-1205.
Buschiazzo et al., 1998, GenBank Acc. No. U83180.1.
Henikoff S, Henikoff JG (1992) "Amino acid substitution matrices from protein blocks." Proc Natl Acad Sci USA 89:10915-10919.
Jantscher-Krenn et al., "The human milk oligosaccharide disialyllacto-N-tetraose prevents necrotising enterocolitis in neonatal rats," 2012, Gut 61:1417-1425.
Kunz C, Rudloff S, Hintelmann A, Pohlentz G, Egge H (1996) "High-pH anion-exchange chromatography with pulsed amperometric detection and molar response factors of human milk oligosaccharides." J Chromatogr B 685: 211-221.

(Continued)

Primary Examiner — Suzanne M Noakes
(74) Attorney, Agent, or Firm — Lisa V. Mueller; Casimir Jones, S.C.

(57) ABSTRACT

The invention provides a mutant enzyme having trans-sialidase activity (EC 3.2.1.18), characterized by an enhanced trans-sialidase:sialidase ratio when compared to its parent sialidase enzyme. Further the enzyme may be used in a method for trans-sialylating mono- and oligo-saccharides, including galacto-oligosaccharides (GOS), fructo-oligosaccharides (FOS), malto-oligosaccharides (MOS), isomalto-oligosaccarides (IMO), lactulose, melibiose, maltose, glycosyl sucrose, lactosucrose and fucose. Trans-sialidated mono- and oligo-saccharides, produced with the mutant enzyme, are useful in preparing infant formula, a prebiotic nutritional supplement, and a food supplement.

15 Claims, 8 Drawing Sheets

Specification includes a Sequence Listing.

(56) References Cited

OTHER PUBLICATIONS

Kunz et al., "Oligosaccharides in HumanMilk: Structural, Functional, and Metabolic Aspects," 2000, Ann. Rev. Nutrition 20:699-722.
Lamsal BP (2012) "Production, health aspects and potential food uses of dairy prebiotic galactooligosaccharides." J Sci Food Agric 92: 2020-2028.
Larkin MA, Blackshields G, Brown NP, Chenna R, McGettigan PA, et al. (2007) "ClustalW and ClustalX version 2." Bioinformatics 23: 2947-2948.
Mäkeläinen H, Saarinen M, Stowell J, Rautonen N, Ouwehand AC (2010) "Xylo-oligosaccharides and lactitol promote the growth of Bifidobacterium lactis and *Lactobacillus* species in pure cultures." Benefic Microb 1: 139-48.
Villa-Kamaroff et al., "A bacterial clone synthesizing proinsulin," 1978, Proc. Natl. Acad. Sci. U.S.A. 75:3727-3731.
Walters DM, Stirewalt VL, Melville SB (1999) "Cloning, Sequence, and Transcriptional Regulation of the Operon Encoding a Putative N-Acetylmarmosamine-6-Phosphate Epimerase (nanE) and Sialic Acid Lyase (nanA) in Clostridium perfringens." J Bacteriol 181: 4526-4532.
Yu ZT, Chen C, Kling DE, Liu B, McCoy JM, et al. (2013) "The Principal Fucosylated Oligosaccharides of Human Milk Exhibit Prebiotic Properties on Cultured Infant Microbiota." Glycobiology 23: 169-177.
Marchler-Bauer A, Lu S, Anderson JB, Chitsaz F, Derbyshire MK, et al. (2011) "CDD: A Conserved Domain Database for the functional annotation of proteins." Nucleic Acids Res 39: D225-D229.
Michalak M, Thomassen LV, Roytio H, Ouwehand AC, Meyer AS, et al. (2012) "Expression and characterization of an endo-1,4-β-galactanase from Emericella nidulans in Pichia pastoris for enzymatic design of potentially prebiotic oligosaccharides from potato galactans." Enzyme Microbl Technol 50: 121-129.
Onumpai C, Kolida S, Bonnin E, Rastall RA (2011) "Microbial utilization and selectivity of pectin fractions with various structures." Appl Environ Microbiol 77: 5747-5754.
Paris G, Cremona ML, Amaya MF, Buschiazzo A, Giambiagi S, et al. (2001) "Probing molecular function of trypanosomal sialidases: single point mutations can change substrate specificity and increase hydrolytic activity." Glycobiology 11: 305-311.
Paris G, Railer L, Amaya MF, Nguyen T, Alzari PM, et al. (2005) "A Sialidase Mutant Displaying trans-Sialidase Activity." J Mol Biol 345: 923-934.
Pereira ME, Zhang K, Gong Y, Herrera EM, Ming M (1996) "Invasive phenotype of Trypanosoma cruzi restricted to a population expressing trans-sialidase." Infect Immun 64: 3884-3892.
Ribeirão M, Pereira-Chioccola VL, Eichinger D, Rodrigues MM, Schenkman S (1997) "Temperature differences for transglycosylation and hydrolysis reaction reveal an acceptor binding site in the catalytic mechanism of Trypanosoma cruzi trans-sialidase." Glycobiology 7: 1237-1246.
Saito T, Itoh T (1992) "Variations and distributions of O-glycosidically linked sugar chains in bovine κ-casein." J Diary Sci 75: 1768-1774.
Schenkman S, Jiang MS, Hart GW, Nussenzweig V (1991) A novel cell surface trans-sialidase of Trypanosoma cruzi generates a stage-specific epitope required for invasion of mammalian cells. Cell 65: 1117-1125.
Schmidt D, Sauerbrei B, Thiem J (2000) "Chemoenzymatic Synthesis of Slatyl Oligosaccharides with Sialidases Employing Transglycosylation Methodology." J Org Chem 65: 8518-8526.
Schrader S, Tiralongo E, Paris G, Yoshino T, Schauer R (2003) "A nonradioactive 96-well plate assay for screening of trans-sialidase activity." Anal Biochem 322: 139-147.
Scudder P, Doom JP, Chuenkova M, Manger ID, Pereira MEA (1993) "Enzymatic Characterization of β-D-Galactoside α2,3-trans-Sialidase from Trypanosoma cruzi." J Biol Chem 268: 9886-9891.
Silva IR, Larsen DM, Meyer AS, Mikkelsen JD (2011) "Identification, expression, and characterization of a novel bacterial RGI Lyase enzyme for the production of bio-functional fibers." Enzyme Microb Technol 49: 160-166.
Singh S, Scigelova M, Hallberg ML, Howarth OW, Schenkman S, et al. (2000) "Synthesis of sialyloligosaccharides using the trans-sialidase from Trypanosoma cruzi: novel branched and di-sialylated products from digalactoside acceptors." Chem Commun 1013-1014.
Skoza L, Mohos S (1976) "Stable thiobarbituric acid chromophore with dimethyl sulphoxide. Application to sialic acid assay in analytical de-O-acetylation." Biochem J 159: 457-462.
Smith LE, Q27064 UniprotKB submitted Jan. 1996 to EMBL/GenBank/DDBJ database.
Smith LE, Uemura, H, Eichinger D. (1996) "Isolation and expression of an open reading frame encoding sialidase from Tiypansoma rangeli." Molecular and Biochemical Parasitology 25 79: 21-33.
Söding J, Biegert A, Lupas AN (2005) "The HHpred interactive server for protein homology detection and structure prediction" Nucleic Acids Res 33: W244-W248.

\* cited by examiner

Figure 2

```
T.rangeli Tr6    TIRERVVHSFRLPTIVNVDGVMVAIADARIETSFDNSFIETAVKYSVDDGATWNTQIAIKN     86
T.cruzi TcTS     --TERVVHSFRLPALVNVDGVMVAIADARIETSNDNSLIDTVAKYSVDDGETWETQIAIKN     85
T.congolense     GTTMRTVHSIRIPSIVEVGGVLMCVGDARYITSEDYFFTDTVAAYSTDGGRTWKREVIIFN    160
T.brucei         ----RTVHSFRIPSFVEVDGVLMGIGDARYITSEDYFFTDTVAKYSADGGKTWKTEVIIEN    183
                                                         * * *

T.rangeli Tr6    SRAS-SVSRVVDPTVIVKGNKLYILVGSFNKTRNIWTQHRDGS----DWEPLIVVGEVTKSA    143
T.cruzi TcTS     SRAS-SVSRVVDPTVIVKGNKLYLVGSINSSRSIWTSHGDAR---DWDILIAVGEVTKST    142
T.congolense     GRVDAHYSRVVDPTVVAKGNNIYLVGRINVTRGIWHNKNNRAGVADWEPFVYKGTVNVGT    221
T.brucei         GRVDPTYSRVVDPTVVAKADSVFVLVARINVTKGIWHNENNAAGIADWEPFMYKGVVTKGA    244
                                                        *   *

T.rangeli Tr6    ANGKTTATISWGKPVSLKPLFPAEFDGILTKEFVGGVGAAIVASNGNLVYPVQIADMGGRV    204
T.cruzi TcTS     AGGKITASIRWGSPVSLKEFPAEMEGMHTNQFLGGAGVAIVASNGNLVYPVQVTNKKKQV    203
T.congolense     KDNATDVSISWER--TAIKSLINFPVSGSPGTQFLGGAGGVVTSNGTIVLPVQARNKANRV    281
T.brucei         DGKTSDVRISWTK-TPLKPLYDFTVAGSKGTQFIGGAGNGVVTLNGTILFPVQARNEDNAV    304
                                                             *******

T.rangeli Tr6    FTKIMYSEDDGNTWKFAEGRSKFGCSEPAVLEWEGKLIINNRVDYN------RRLVYESS    258
T.cruzi TcTS     FSKIFYSEDEGKTWKFGKGRSAFGCSEPVALEWEGKLIINTRVDYR------RRLVYESS    257
T.congolense     VSMILYSADDGKSWHFGKGEAGVGTSERAALTEWDGKLLISARSDGG-----QGYRMIFESS    337
T.brucei         VSMVMYSVDDGVSWHFARGETALLTSEASLTEWNGKLLMSARTDTSGVNVEGGEFRKVFESN    365
                                         ▲ *

T.rangeli Tr6    DMGKTWVEALGTLSHVWTNSPTSNQP--------DCQSSFVAVTIEGKRVMLFTHPLNLKGR    312
T.cruzi TcTS     DMGNSWLEAVGTLSRVWGPSPKSNQP--------GSQSSFTAVTIEGMRVMLFTHPLNFKGR    311
T.congolense     DLGATWKEMLNSISRVIGNSPGRSGP-------GSSSGFITVTVEGVPVMLLTHPKNLKGS    391
T.brucei         NLGATWEESLGTISRVIGNSPDRTKPSTANPGSSGALITVTLGDVPVMLITHPKNTKGA    426

T.rangeli Tr6    WMRDRLHLWMTDNQRIFDVGQISIGDENSGYSSVLYKDD-KLYSLHEINTNDVYSLVFVRL    372
T.cruzi TcTS     WLRDRLNLWLTDNQRIYNVGQVSIGDENSAYSSVLYKDD-KLYCLHEINSNEVYSLVFARL    371
T.congolense     YYRDRLQMWMTDGNRAWHVGQVSEGDDNSAYSSLLYTPDGVLYCLHEQNIDEVYS-----    446
T.brucei         WSEDRLQLWMTDGNRAWLVGQISEGDDNSAYSSLLLARDGLLYCLHEQNIDEVYG-----    481
                                                         *
```

MUTANT SIALIDASE HAVING TRANS-SIALIDASE ACTIVITY FOR USE IN PRODUCTION OF SIALYLATED GLYCANS

CROSS-REFERENCE TO RELATED APPLICATIONS

This is a U.S. national stage entry of International Patent Application No. PCT/EP2014/057422, filed on Apr. 11, 2014, which claims priority to European Patent Application No. 13163551.8, filed on Apr. 12, 2013, the entire contents of all of which are fully incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 74,659 Byte ASCII (Text) file named "P1419US00-030547-9041-US00-SEQ-LIST-01-16-18.txt" created on Jan. 15, 2018.

FIELD OF THE INVENTION

The invention relates to enzymes having trans-sialidase activity (EC 3.2.1.18), that are derived from Trypanosomal sialidases by mutation. The enzymes obtained by mutation find particular use in the production of diverse sialylated galacto-oligosaccharides (GOS) and fructo-oligosaccharides (FOS), these being important additives in infant formula, a prebiotic nutritional supplement, and a food supplement.

BACKGROUND OF THE INVENTION

Prebiotics are dietary substances that stimulate growth of selected groups of microorganisms in the colon and in addition may have other health benefits. Galactooligosaccharides (GOS), fructooligosaccharides (FOS), lactulose, and isomaltooligosaccharides (IMO) are among the few well-established prebiotics. In human milk, oligosaccharides constitute the third largest component, present in amounts as much as 20-25 g/l around parturition, later declining to 5-15 g/L. With few exceptions, all known human milk oligosaccharides (HMOs) have a lactose core and are elongated via linkage to one or more units of galactose and N-acetylglucosamine, and can be decorated with several sialic acid and fucose residues. More than 100 different such glycan structures have been identified and approximately 10-20% of these are sialylated (Bode, 2012, *Glycobiology* 22(9): 1147-1162). Sialylation and/or fucosylation of many of these HMOs appear to convey important functional properties. For example, HMOs can bind human pathogens, such as, *Escherichia coli* K1, *Haemophilus influenzae, Pasteurella multocida, Neisseria meningitidis, Campylobacter jejuni, Vibrio cholerae, Helicobacter pylori* and *Streptococcus agalactiae* and thereby reduce the incidence of diarrhoea and other diseases in infants. This ability of HMOs to function as soluble decoy receptors for human pathogens is most likely enhanced by their diversity, since mannose-containing glycoproteins, sialylated and fucosylated glycans each target different subsets of pathogens (Kunz et al., 2000, *Ann. Rev. Nutrition* 20:699-722). In addition, sialylated HMOs may modulate the immune system; for example T cell cytokine production is stimulated by sialylated HMOs in vitro (Eiwegger et al., 2004, *Pediatric Rev.* 56:536-540). In most cases, the active HMO molecules have not been identified, but in the case of necrotising enterocolitis, a frequent and often fatal disease in infants, the protective effect was recently shown to be due to a single molecule, disialyllacto-N-tetraose, using a rat model (Jantscher-Krenn et al., 2012, *Gut* 61:1417-1425).

Bovine milk, which forms the basis for most infant formula, has a very low oligosaccharide content when compared with human milk, with a different sialylation and fucosylation profile. In an attempt to mimic the composition of human milk, milk formula is currently supplemented with (non-HMO) GOS and FOS. However, due to their lack of sialic acid residues, the added GOS and FOS are unlikely to provide the therapeutic benefits of HMOs, described above (Bode, 2012, supra).

Efforts to sialylate GOS and FOS rely on glycan sialylation, which can be achieved chemically as well as enzymatically using different types of enzymes [1]. For example, a trans-sialidase enzyme (TcTS) from *Trypansoma cruzi*, the causative agent of Chagas disease, has been used to transfer sialic acid from a donor to an acceptor glycan [2]. However, in the context of industrial production of food-grade HMOs, the *T. cruzi* trans-sialidase has a major drawback, namely that it constitutes an important virulence factor within *T. cruzi* [3].

A native sialidase (TrSA) found in the non-pathogenic *Trypansoma rangeli*, has been used as a starting point for generating mutant enzymes that possess trans-sialidase activity [4]. Although this sialidase shares 70% sequence identity with that of TcTS, and has the same overall tertiary structure, it is a strict hydrolase having no detectable trans-sialidase activity [4]. The sialidase, TrSA, and the trans-sialidase, TcTS, share a common double displacement mechanism with a tyrosine as catalytic nucleophile [5] [6]. In TcTS, the acceptor binding site consists of Tyr119 and Trp312 forming stacking interactions with the acceptor sugar [7]. In TrSA, Trp313 (corresponding to Trp312 in TcTS) is found in a different conformation due to a Gln at position 284, while it has a Ser residue at position 120 corresponding to Tyr119 in TcTS [8]. In addition to these differences in the acceptor binding site, a conserved Asp96 hydrogen bonds differently to sialic acid in the two enzymes, possibly due to two residue differences, Val96Met and Pro98Ala. Initial attempts based on TrSA single point mutants, failed to generate an enzyme with any trans-sialidase activity. Subsequent studies revealed the need for a combination of 5 point mutations TrSA, comprising Ser120Tyr, Gly249Tyr, and Gln284Pro at the acceptor-binding site as well as Met96Val, and Ala98Pro at the sialic acid binding pocket to confer trans-sialidase activity (1% of TcTS) to TrSA. An additional single mutation Ile37Leu increased the levels of trans-sialidase activity to 10% of a *T. cruzi* trans-sialidase [4]. Furthermore, kinetic data indicate that these TrSA mutants display a >25-fold lower affinity for lactose and >100-fold higher turnover (kcat) for the undesired, competing hydrolysis compared to TcTS [4] indicating a considerable need for improvement before such an enzyme would have any practical value for trans-sialylation.

Despite the relatively close sequence homology between TrSA and TcTS, there is no evidence that the native sialidase expressed by *Trypansoma rangeli* has any trans-sialidase activity. Isolation and expression of a TrSA gene from *Trypansoma rangeli* is reported by Smith et al [31]. The isolated TrSA gene encodes an inactive protein, likely due to the substitution of a strictly conserved arginine, that functions by coordinating the carboxyl of sialic acid, by a cysteine residue [31]. Smith et al., also submitted a TrSA gene encoding sialidase (Q08672) to GenBank, which is predicted to be an anhydrosialidase [32]. In addition to lacking the Arg residue required for coordinating the carboxyl of sialic acid, this sialidase (Q08672) lacks the mutations S119Y and Q284P that are required to establish the acceptor binding site, and for this reason cannot function as a trans-sialidase.

Buschiazzo et al., [33] report the isolation of a *Trypanosoma rangeli* gene that is predicted to encode a TrSA, UNIPROT: Q08672 having 70% sequence identity to TcTS, which is a common feature of other TrSAs having only hydrolytic activity. One amino acid substitution in the primary sequence of a TrSA, found essential for obtaining a mutant TrSA having measurable trans-sialiase activity is Gly249-Tyr, which decreases hydrolytic activity [4]. A second mutation, Ile-37Leu, which in combination with Tyr120, significantly enhances trans-sialidase activity in this mutant [4]. Neither of these mutations is found in TrSA, UNIPROT: Q08672.

In human milk, lactose or HMOs of various lengths can be sialylated in α2-3 or α2-6 linkage which can be added to a terminal galactose or a subterminal N-acetyl-glucosamine, thereby contributing to the diversity of HMOs present. Efforts to mimic such complex oligosaccharide compositions require a trans-sialidase that can transfer sialic acid to a variety of different acceptor groups. Although it is well established that TcTS can sialylate the terminal galactose of a glycan, there is no documented evidence of a trans-sialidase that can use other acceptor groups, which is essential if the diversity of HMOs is to be obtained synthetically.

Accordingly, there remains a need for an enzyme having trans-sialidase activity, that is neither a virulence factor nor derived from a pathogenic organism; and further has no significant sialidase hydrolytic activity, and that can transfer a sialic acid moiety to a range of different acceptor groups present in a glycan molecule.

SUMMARY OF THE INVENTION

According to a first embodiment, the invention provides a mutant polypeptide having at least 80% amino acid sequence identity to amino acids residues 28-372 of SEQ ID NO: 2, and wherein residues 197 to 203 of SEQ ID NO. 2 comprise one or more of substituted amino acid residues resulting in a net positive charge of at least +3 for residues 197 to 203 of SEQ ID NO. 2, and wherein amino acid residues 37, 96, 98, 120, 249, 284 in the sequence of the mutant polypeptide have 100% sequence identity to the corresponding amino acid residues in SEQ ID NO. 2, wherein the polypeptide has trans-sialidase activity (EC 3.2.1.18). A net positive charge of at least +2, preferably +3, for residues 197 to 203 of SEQ ID NO. 2 in the polypeptide of the invention confers a reduced hydrolase activity when compared to the polypeptide having the sequence of amino acids residues 28-372 of SEQ ID NO: 2. The mutant polypeptide may be obtainable by mutation of SEQ ID NO: 2, and the amino acid sequence of the polypeptide may have sequence identity with SEQ ID NO: 2 with the exception that residues 197 to 203 of SEQ ID NO. 2 comprise one or more of substituted amino acid residues resulting in a net positive charge of at least +2, preferably +3, for residues 197 to 203.

According to a second embodiment, the mutant polypeptide additionally comprises a C-terminal linker and carbohydrate-binding domain selected from among: a) C-terminal linker peptide and carbohydrate-binding peptide of *Trypanosoma rangeli* trans-sialidase comprising amino acid residues 373 to 638 of SEQ ID NO: 2; b) C-terminal linker peptide and carbohydrate-binding peptide of *Trypanosoma cruzi* trans-sialidase (SEQ ID NO. 8); c) C-terminal linker peptide and carbohydrate-binding peptide of *Trypanosoma congolense* trans-sialidase (SEQ ID NO. 9); d) C-terminal linker peptide and carbohydrate-binding peptide of *Trypanosoma brucei* trans-sialidase (SEQ ID NO. 10).

The mutant polypeptide may be expressed as a fusion protein comprising a homologous or heterologous amino-terminal signal peptide and/or a heterologous amino-terminal or carboxy-terminal peptide having selective substrate binding affinity for purification of the polypeptide.

According to a further embodiment, the invention provides a DNA molecule comprising a positive DNA strand having a nucleic acid sequence encoding the mutant polypeptide according to the first or second embodiment.

According to a further embodiment, the DNA molecule may have a nucleotide sequence encoding the mutant polypeptide having an amino acid sequence selected from among: a) amino acid residues 48-372 of SEQ ID NO. 4; b) amino acid residues 21-372 of SEQ ID NO. 4; c) amino acid residues 48-638 of SEQ ID NO. 4; and d) amino acid residues 21-638 of SEQ ID NO. 4.

According to a further embodiment, the invention provides a recombinant host cell comprising the DNA molecule encoding the mutant polypeptide, wherein said cell is prokaryotic or eukaryotic and selected from among a bacterial cell, a yeast cell and a fungal cell. The DNA molecule may either be integrated into the genome of the host cell or it may be integrated into a self-replicating plasmid in the host cell.

According to a further embodiment, the invention provides a method for producing the mutant polypeptide of the invention comprising the steps of:
a) providing a recombinant host cell, wherein the cell comprises a DNA molecule, the DNA molecule comprising a nucleic acid sequence encoding the mutant polypeptide of the invention, and b) incubating the host cell in a medium in which the host cell is capable of expressing the mutant polypeptide, and c) recovering the mutant polypeptide expressed by the host cell in step a) from the medium.

According to a further embodiment, the invention provides an enzyme composition comprising the mutant polypeptide of the invention, wherein the composition is formulated as a dry powder, a tablet, or as a liquid.

According to a further embodiment, the invention provides a method for producing sialylated mono- and/or oligosaccharides, comprising the steps of:
a) providing a sialic acid donor molecule and a molecule comprising an acceptor mono- and/or oligo-saccharides capable of trans-sialylation; b) contacting the molecules of (a) with the mutant polypeptide of the invention in an aqueous solution.

According to a further embodiment, the invention provides a composition comprising sialylated mono- and oligosaccharides produced by the method of the invention, wherein the composition is selected from an infant formula, a prebiotic nutritional supplement, and a food supplement.

BRIEF DESCRIPTION OF THE DRAWINGS

FIG. 2. Sequence alignment of sialidase catalytic domain from Tr6 (TrSA$_{Smut}$ [PDB: 1WCS] with a 6th point mutation, I37L; amino acid residues 26-372 of SEQ ID NO. 2) and related trans-sialidases. Tr6 and trans-sialidases from *T. cruzi* (SEQ ID NO. 5), *Trypanosoma congolense* (SEQ ID NO. 6) and *Trypanosoma brucei* (SEQ ID NO. 7) were aligned using ClustalW. Amino acids within 14 Å of sialic acid binding site are shown in bold. The seven amino acid motif is indicated with filled circles, reverting mutations are indicated with a triangle while other mutated sites are indicated with asterisks.

DETAILED DESCRIPTION OF THE INVENTION

Figure 1A:
FIG. 1. A. Domain structure of a sialidase enzymes (EC 3.2.1.18), as exemplified by *Trypanosoma cruzi* trans-sialidase (TcTS). The catalytic domain is located on the left (light gray), the carbohydrate-binding domain to the right (dark grey), the two domains are linked together by a peptide linker (black). A ligand (sialyllactose) bound in the active site is shown in black sticks. B. Cartoon of mutant trans-sialidase of the invention, showing domain structure (catalytic domain peptide; linker peptide; lectin peptide (carbohydrate-binding domain)) and one example of the mutated motif (amino acids 197-203), and amino acid residue positions with respect to SEQ ID NO: 2.
Figure 1B:
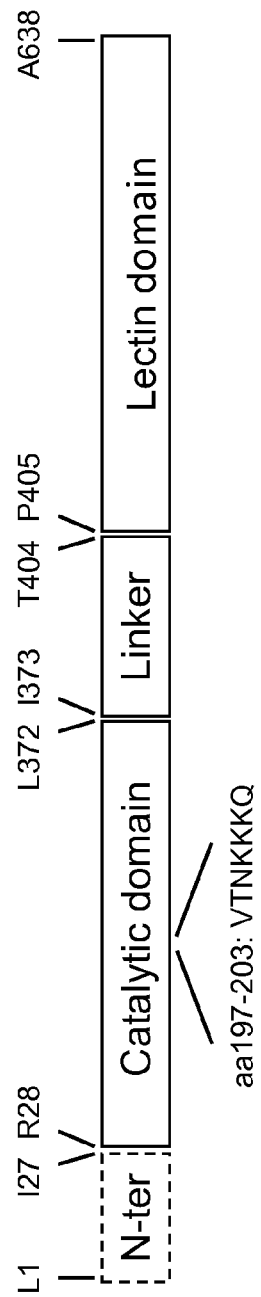

A common structural feature of sialidase enzymes (EC 3.2.1.18) is their six bladed β-propeller catalytic domain with an active site comprising a catalytic arginine triad that coordinates sialic acid via the carboxylate group, an Asp residue as acid/base catalyst, and a Tyr/Glu nucleophile pair (FIG. 1). The catalytic domain can additionally be functionally linked to a non-essential carbohydrate-binding module (CBM) that may serve to recognize sialic acid and/or assist the enzyme target its substrate on cell surfaces. *Micromonospora viridifaciens* secretes two forms of sialidase from the same gene, a short form, with just the catalytic domain, and a longer form with a galactose-binding module, dependent on the food source [29].

I a Mutant Trans-Sialidase Derived from a *Trypanosoma rangeli* Sialidase

I.i Structure of Mutant Trans-Sialidase Comprising a Catalytic Domain

The present invention provides a mutant enzyme (EC 3.2.1.18) having an enhanced trans-sialidase: sialidase activity ratio relative to its immediate parent enzyme, the mutant being ultimately derived from a sialidase from *Trypanosoma rangeli* (GenBank Acc. No: U83180.1). In a first embodiment, the mutant enzyme is a polypeptide comprising at least a catalytic domain having trans-sialidase activity. The amino acid sequence of the catalytic domain has at least 60%, 65%, 70%, 75%, 80%, 85%, 90%, 95%, 98% or 99% sequence identity to amino acids residues 28-372 of SEQ ID NO. 2, and one or more amino acid residues are substituted with respect to amino acid residues 197 to 203 (amino acid motif) of SEQ ID NO. 2, to give a mutant amino acid motif that has a net positive charge of at least +2, preferably +3. Expression of the mutant enzyme yields a mature enzyme comprising a catalytic domain alone, having trans-sialidase activity (FIG. 1). The location of the catalytic domain in SEQ ID NO: 2 was confirmed using NCBI Conserved Domain Search.

The amino acid motif consisting of amino acid residues 197 to 203 of SEQ ID NO: 2 has the sequence IADMGGR, which has one positively charged amino acid (R) and one negatively charged amino acid (D), giving a net charge=0. A mutant motif having a net positive charge of +2 or +3 that can be obtained by the substitution of one or more amino acid residues selected from among 198-203 of SEQ ID NO: 2, wherein the selected residue is substituted with a positively charged amino acid residue, and/or the substitution of residue 199 (D) with a neutral or positively charged amino acid. A suitable positively charged amino acid is a K or R. A suitable neutral amino acid to substitute for residue 199 (D) may be selected from among polar neutral amino acids including asparagine, glutamine, glycine, serine, threonine, cysteine, and tyrosine, or a nonpolar (hydrophobic) amino acids such as include alanine, leucine, isoleucine, valine, proline, phenylalanine, tryptophan and methionine.

For example, the mutant motif may have any amino acid sequence selected from among: IAXMGGR; IXZMGGR; IAZXGGR; IAZMXGR; IAZMGXR, where X is K or R and wherein Z is a neutral amino acid, for example N, wherein the motif has a net positive charge of +2.

Alternatively, the mutant motif may have any amino acid sequence selected from among: IXDXGGR; IXDMXGR; IXDMGXR; IADXXGR; IADMXXR, where X is K or R and wherein Z is a neutral amino acid, for example N, wherein the motif has a net positive charge of +2.

Furthermore, the mutant motif may have any amino acid sequence selected from among: IXZXGGR; IAZXXGR; IAZMXXR; IAXMGXR; IAXMXGR; IAXXGGR; and IAZXXXZ where X is K or R and wherein Z is a neutral amino acid, for example N, wherein the motif has a net positive charge of +3.

Furthermore, the mutant motif may have any amino acid sequence selected from among: VTNKKKQ (SEQ ID NO.: 58), ARNKANR (SEQ ID NO.: 59), IANKKKQ (SEQ ID NO.: 60), and IANRRRQ (SEQ ID NO.: 61). Thus according to one example, the mutant enzyme is a polypeptide comprising a catalytic domain corresponding to amino acids residues 28-372 of SEQ ID NO: 4, wherein the motif consisting of amino acid residues 197 to 203 has a positive charge of +3.

The mutant enzyme of the present invention differs from the sialidase of *Trypanosoma rangeli* (GenBank Acc. No: U83180.1) by an additional 6 point mutations located within the catalytic domain. These 6 point mutations in *T. rangeli* sialidase were previously disclosed by Paris et al., 2005 [4]. Thus the immediate parent enzyme, from which the present mutant enzyme was derived, has the protein sequence of $TrSA_{Smut}$ (Protein Data Bank file: 1WCS) that further includes I37L as the $6^{th}$ point mutation (corresponding to SEQ ID NO: 2).

I.ii Structure of Mutant Trans-Sialidase Comprising a Catalytic Domain and a Carbohydrate-Binding Peptide (Lectin-Domain) Connected by a Linker Peptide In a second embodiment, the mutant enzyme is a polypeptide comprising a catalytic domain according to the first embodiment (corresponding to amino acids residues 28-372 of SEQ ID NO: 2, wherein one or more amino acid residues within a motif consisting of amino acid from residue 197 to 203 of SEQ ID NO. 2 is mutated, wherein the mutant motif has a net positive charge of at least +2, preferably +3, as well as a C-terminal carbohydrate-binding domain where the two domains are linked by a linker peptide. The carbohydrate-binding domain and linker peptide (comprising a non-catalytic region) has an amino acid sequence having at least 25%, 30%, 35%, 40%, 45%, 50%, 55%, 60%, 65%, 70%, 75%, 80%, 85%, 90%, 95%, or 98% sequence identity to amino acid residues 373-638 of SEQ ID NO: 2. The C-terminal carbohydrate-binding domain folds separately from the catalytic domain, in a β-sandwich fold, leaving the two domains to interact through a hydrophobic interface.

Examples of the second embodiment include the mutant enzyme wherein the C-terminal domain is derived from a Trypanosomal trans-sialidase or sialidase enzyme. For example, the C-terminal domain may be selected from among: C-terminal amino acid residues 373 to 638 of SEQ ID NO: 2 derived from Tr6 mutant *T. rangeli* sialidase; C-terminal linker peptide and carbohydrate-binding peptide having SEQ ID NO. 8, derived from amino acid residues 373 to 642 of *T. cruzi* trans-sialidase [Uniprot ID Q26966]; C-terminal linker peptide and carbohydrate-binding peptide having SEQ ID NO. 9, derived from amino acid residues 452 to 702 of *T. congolense* trans-sialidase [Uniprot IDG0WJG3]; C-terminal linker peptide and carbohydrate-binding peptide having SEQ ID NO. 10, derived from amino acid residues 373 to 642 of *T. brucei* trans-sialidase (Uniprot ID [Q57XJ2].

Optionally, the mutant enzyme according to the first or second embodiment is a polypeptide comprising an N-terminal peptide region fused to the catalytic domain corresponding to amino acids residues 1-372 of SEQ ID NO: 2. According to one example of the second embodiment, the mutant enzyme is a polypeptide comprising amino acids residues 28-638 of SEQ ID NO: 4 or amino acids residues 1-638 of SEQ ID NO: 4.

I.iii the Mutant Amino Acid Motif in the Mutant Trans-Sialidase Confers an Enhanced Trans-Sialidase:Sialidase Activity Ratio and Sialylated Product Yield The *T. rangeli* sialidase mutant enzymes, previously described by Paris et al., 2005 [4], had the major deficiency that they retained the hydrolytic catalytic properties of the parent *T. rangeli* sialidase from which they were derived. The mutant enzyme of the present invention according to the first or second embodiment, comprise a mutant motif (as defined in I.i and I.ii) having a net positive charge of at least +2. Mutations creating this mutant motif greatly reduce the hydrolase activity of the parent sialidase enzyme (see Example 3.3; FIG. 5A).

The catalytic effect of the mutant motif was surprising since the motif is relatively far removed from the acceptor binding site (~14 Å), and is therefore unlikely to affect acceptor binding directly. The net positively charged motif, which is located at the border of the binding cleft, may change the electrostatic field in the cleft, creating an increased hydrogen bond donor capacity that could potentially disrupt or even reverse the water network in the active site. Hydrolysis requires a water network aligned with oxygen lone pairs towards the sialic acid. Thus, introduction of a strong positive charge (e.g. at least +2) and hydrogen-donor tendency at the edge of the binding cleft may turn the oxygen lone pairs towards the field of the lysines and correspondingly impair the nucleophilicity of the water network in the cleft. Such a disruption of the water network could provide the theoretical explanation for the exquisite quenching of hydrolysis, not achieved by other sialidase mutants.

The mutant trans-sialidase has a high trans-sialylation product yield when assayed under optimal conditions due to its very low hydrolase activity (see Example 4).

I.iv the Mutant Trans-Sialidase has Broad Acceptor-Substrate Specificity

The mutant trans-sialidase of the invention has unexpectedly broad acceptor-substrate specificity, in contrast to native TcTS, which is only known to act on acceptor substrates comprising a terminal galactose [24]. The mutant trans-sialidase is both able to trans-sialylate terminal galactose as well as terminal glucose and even monomers of glucose and fucose. Importantly, the mutant enzyme was also able to trans-sialylate GOS and IMO and lactulose preparations in reasonable yields (Example 5; Table 2). The sialylated GOS and IMO products obtained using the mutant trans-sialidase are complex, indicating that oligosaccharides of different chain length in the GOS and IMO mixtures are sialylated. In view of its broad acceptor-substrate specificity, the mutant trans-sialidase is particularly suitable for enzymatic sialylation of a broad range of glycans in the manufacture of functional food ingredients and prebiotics. GOS and IMO and lactulose are well-documented prebiotic compounds used as a nutritional supplement.

Additionally, the mutant trans-sialidase is able to use casein glycomacropeptide (cGMP), which is a side-stream from dairy industry, as sialic acid donor (Example 5, FIG. 5). In summary, the mutant enzyme of the invention, is characterized by both a high trans-sialidase:sialidase activity ratio and a remarkably broad acceptor-substrate specificity, while having the additional advantages of neither being derived from a non-pathogenic host, nor being a virulence factor.

II a Method for Production of the Mutant Trans-Sialidase of the Invention, Including Expression Vectors and Host Cells IIi Expression Constructs for Production of a Mutant Trans-Sialidase The invention further provides DNA molecules comprising a positive DNA strand having a nucleic acid sequence encoding the mutant trans-sialidase according to the first and second embodiment. For the purposes of expression in a selected host cell, the mutant trans-sialidase may be expressed as an N-terminal translational fusion protein, having an N-terminal homologous or heterologous amino-terminal peptide comprising a signal peptide sequence and optionally followed by a protease cleavage site. A suitable N-terminal fusion protein may include α-factor signal sequence and Kex2 and/or Ste3 protease recognition sequences.

For the purposes of purification of the expressed protein, the mutant trans-sialidase may be expressed as a translational fusion protein comprising a heterologous peptide having selective substrate binding affinity suitable for purification of the polypeptide, as for example c-myc and 6xHis-tag, as present in SEQ ID NO: 12. The heterologous peptide may be located either N-terminal or carboxy-terminal to the mutant trans-sialidase in the fusion protein, either in addition to/or independently of an N-terminal signal peptide.

According to an embodiment, the invention provides a DNA molecule encoding the mutant trans-sialidase selected from among: a nucleotide sequence encoding a catalytic domain comprising amino acids residues 28-372 of SEQ ID NO: 4; a nucleotide sequence encoding an N-terminal peptide region fused to the catalytic domain comprising amino acids residues 1-372 of SEQ ID NO: 4; a nucleotide sequence encoding the catalytic domain linked to a carbohydrate-binding domain comprising amino acid residues 28-638 of SEQ ID NO: 4; and a nucleotide sequence encoding an N-terminal peptide region fused to the catalytic domain linked to a carbohydrate-binding domain comprising amino acid residues 1-638 of SEQ ID NO: 4.

For example, the DNA molecule encoding the mutant trans-sialidase may be selected from among: nucleotide sequence 84-1116 of SEQ ID NO: 3 encoding the catalytic domain comprising amino acids residues 28-372 of SEQ ID NO: 4; nucleotide sequence 1-1116 of SEQ ID NO: 3 encoding an N-terminal peptide region fused to the catalytic domain comprising amino acids residues 1-372 of SEQ ID NO: 4; nucleotide sequence 84-1914 of SEQ ID NO: 3 encoding the catalytic domain linked to a carbohydrate-binding domain comprising amino acid residues 28-638 of SEQ ID NO: 4; nucleotide sequence 1-1914 of SEQ ID NO: 3 encoding an N-terminal peptide region fused to the catalytic domain linked to a carbohydrate-binding domain comprising amino acid residues 1-638 of SEQ ID NO: 4.

The DNA molecules encoding the mutant trans-sialidase to be expressed are cloned into a suitable self-replicating or genome-integrating vector (plasmid) or are PCR amplified for the purpose of introducing the DNA molecules into a suitable expression host cell. Where the DNA molecule is cloned into vector, the DNA molecule will be cloned behind a DNA promoter, whereby the nucleotide sequence of the promoter is operably linked to the nucleic acid sequence encoding the mutant trans-sialidase. Suitable promoter elements for expression in yeast or other fungi include the Gal 4 promoter, the ADC (alcohol dehydrogenase) promoter, alcohol oxidase promoter (AOX), PGK (phosphoglycerol kinase) promoter, alkaline phosphatase promoter, while promoters for prokaryotic expression vectors include the p-lactamase promoter (Villa-Kamaroff et al., 1978, Proc. Natl. Acad. Sci. U.S.A. 75:3727-3731).

IIii Expression Hosts Comprising Mutant Trans-Sialidase Expression Constructs

Suitable expression hosts include bacterial (e.g. *Escherichia coli; Bacillus subtilis; Bacillus licheniformis*); yeast (e.g. *Saccharomyces cerevisiae; Pichia pastoris, Hansenula polymorpha*) or fungal (*Aspergillus niger, A. oryzae, Trichoderma viridae*) hosts. DNA molecules, encoding the mutant trans-sialidase to be expressed, may be introduced into a host cell by transformation employing standard protocols known in the art, for example by electroporation. Preferably the mutant trans-sialidase is fused with a signal peptide, facilitating secretion of the expressed protein and its subsequence purification from the host cultivation medium.

The invention provides a method for producing the mutant trans-sialidase comprising the steps of providing a recombinant host cell, wherein the cell comprises a DNA molecule encoding the mutant trans-sialidase according to the first or second embodiment, and incubating the host cell in a medium in which the cell is capable of expressing the mutant trans-sialidase, for example a growth medium, and then recovering the mutant trans-sialidase expressed by the host cell from the host cell cultivation and/or incubation medium.

IIiii Methods for Detecting and Measuring the Specific Activity of the Mutant Trans-Sialidase The invention provides a method for assaying the mutant trans-sialidase of the invention, that may for example be obtained by recombinant expression. Example 2.1 describes a fluorescence-based assay employing cGMP-bound sialic acid (for example 1 mM) as donor substrate and methylumbelliferyl-β-D-galactopyranoside (MU-Gal) as the acceptor (for example 0.5 mM), where the reaction is performed in a 50 mM phosphate-citrate (pH 6) at 30° C.

The trans-sialylation:sialidase activity ratio of an enzyme of the invention can be determined by measuring and determining the ratio of the initial reaction rate of the enzyme for the trans-sialidase reaction with respect to the sialidase reaction as described in Example 2.1 and 2.2.

III Methods for Producing a Product Comprising Sialylated Mono- or Oligo-Saccharides The invention further provides a method for producing a product comprising sialylated mono- or oligo-saccharides (glycan), comprising the steps of: providing a sialic acid donor molecule and a molecule comprising an acceptor (e.g. glycan) capable of trans-sialylation; providing a mutant trans-sialidase according to the first or second embodiment; contacting the mutant trans-sialidase with both of the donor and acceptor molecules in an aqueous solution.

A suitable sialic acid donor molecule includes cGMP-bound sialic acid. One source of cGMP is a side-stream (e.g. cheese-processing waste stream) from the dairy industry. Other sources include fetuin, colominic acid and free sialic acid. Whey containing sialic acids, is a byproduct obtained when cheese or rennet casein is produced from milks such as cow milk, goat milk, and sheep milk. For example acid whey, is generated by separating the solids when skim milk is coagulated to form cottage cheese. A cheese processing waste stream is the portion of cheese manufacturing not retained for cheese after formation of curd. The cheese processing waste stream typically refers to the fluid drained from curd, which is frequently discarded. A cheese processing waste stream can be whole whey, demineralized whey permeate, the regeneration stream from demineralized whey permeate, whey permeate, whey powder.

A suitable acceptor glycan capable of trans-sialylation includes galacto-oligosaccharides (GOS), fructo-oligosaccharides (FOS), malto-oligosaccharides (MOS), isomalto-oligosaccarides (IMO), lactulose, melibiose, maltose, glycosyl sucrose, lactose, lactosucrose, Lacto-N-tetraose (LNT), Lacto-N-neotetraose (LnNT), Lacto-N-fucopentaose I (LNFP I), and Lacto-N-fucopentaose V (LNFP V) and fucose.

Optimal substrate concentrations for use in producing sialylated products using the expressed trans-sialidase of the invention may be determined for each selected acceptor substrate. The sialyloligosaccharides produced according to the methods of the invention may be recovered using methods known in the art, including, but not limited to, ultrafiltration, diafiltration, electrodialysis, ion-exchange chromatography and phase partition chemistry.

IV Methods for Producing a Product Comprising Sialylated Galacto-Oligosaccharides The invention further provides a two-step method for producing sialylated GOS comprising the steps of: providing a source of lactose, contacting the lactose with a β-galactosyltransferase capable of transferring a galactose residue from lactose to an acceptor molecule capable of extension by transgalactosylation (e.g. lactose or a GOS); followed by the step of combining the product of trans-galactosylation with a sialic acid donor molecule (as described herein) to provide a mixture; and then contacting the mixture with a mutant trans-sialidase according to the first or second embodiment to produce a sialylated GOS product. An additional step of enrichment and purification of the products of transgalactosylation (i.e. GOSs) may be included prior to performing the step of trans-sialylation with the mutant trans-sialidase. The suitable 3-galactosyltransferase is a type of glycosyltransferase (EC.2.4.1) which catalyzes the transfer of galactose, such enzymes being well-known in the art [30].

V Sialylated Mono- or Oligo-Saccharides and Compositions Thereof

The invention further provides a sialylated mono- and/or oligosaccharide product or a composition comprising the product, obtained by treating a mono- and/or oligosaccharide substrate with the trans-sialidase of the invention. Compositions comprising the sialylated mono- and/or oligosaccharide products may include infant formula, a prebiotic nutritional supplement or a food supplement.

In the present context, infant formula means a foodstuff comprising the sialylated mono- and/or oligosaccharide product, obtained or obtainable by the method of the present invention, which is suitable for nutritional use by infants during the first 4-6 months or even 4 to 12 months of life and satisfying by itself the nutritional requirements of infants. In the present context, a prebiotic food supplement uses the sialylated mono- and/or oligosaccharide product, obtained or obtainable by the method of the present invention, to enhance the beneficial effects and efficiency of probiotics, such as *Lactobacillus* and *Bifidobacterium* species, for example by promoting the development of an early bifidogenic intestinal microbiota in infants, in reducing the risk of development of allergy and/or asthma in infants, in preventing and treating pathogenic infections in such as diarrhoea in infants. In the present context, the food supplement is a digestive health functional food used with the intention to enhance and preserve digestive health, and avoid digestive disorders, by utilizing the sialylated mono- and/or oligosaccharide product, obtained or obtainable by the method of the present invention, as physiologically functional ingredients or components in the form of a liquid, tablets, capsules, or powder.

EXAMPLES

Example 1 Cloning and Expression of *T. rangeli* Sialidase Gene Mutants in Yeast 1.1 Construction of Vector Comprising Parent Sialidase Gene (pPICZα-Tr6)

A gene encoding a polypeptide comprising a *T. rangeli* sialidase (PDB 1WCS; SEQ ID NO. 1) with the following mutations, M96V, A98P, S120Y, G249Y, Q284P and I37L [12] was codon-optimized and synthesized by DNA 2.0 (Menlo Park, Calif., United States of America). The synthetic gene was inserted into PICZαC vector (Invitrogen) between the XbaI and XhoI restriction sites generating a gene (SEQ ID NO: 11) encoding a translational fusion comprising the mutant trans-sialidase (SEQ ID NO: 13) having a N-terminal α-factor signal sequence followed by Kex2 and Ste3 protease recognition sites (SEQ ID NO: 12), and a C-terminal c-myc and 6xHis tag (SEQ ID NO: 14). The encoded mature polypeptide has 662 amino acids, following removal of the signal peptide and protease recognitions sites, and a theoretical molecular mass of 73 kDa. The plasmid vector was propagated in *Escherichia coli* NM522 grown at 37° C. with shaking in low salt LB (10 g/L tryptone, 5 g/L yeast extract and g/L NaCl) supplemented with 25 μg/mL zeocin.

1.2 Mutation of Parent Gene (Tr6)

The vector, pPICZa-Tr6, was used as template for introduction of additional mutations by PCR using overlapping primers (Table 1) employing standard PCR mutation protocols. PCR products were inserted in pPICZaC between the XhoI and XbaI sites. Constructs were sequenced to confirm the mutations and to assure that no unwanted mutations had been introduced by PCR. The mutants of Tr6 are denoted by the amino acid change compared to the parent (e.g. Tr6 Q123R), except for a multi-mutant denoted Tr13 where amino acids 197-203 were changed from IADMGGR (SEQ ID NO.: 62) to VTNKKKQ (SEQ ID NO.: 58).

TABLE 1

| Name | Sequence | SEQ ID NO. |
|---|---|---|
| Tr_fwd | GCTCTCGAGAAGAGAGAGGCTGAAG | 15 |
| Tr_rev | CGCTCTAGAAATGCTGCTGTACCAGC | 16 |
| Q123S_F | CTATTGGACCTCTCACAGAGATGGATCTGACTGG | 17 |
| Q123S_R | CATCTCTGTGAGAGGTCCAATAGTTCCTTGTCTTG | 18 |
| R125G_F | GACCCAGCACGGAGATGGATCTGACTGGGAACC | 19 |
| R125G_R | CAGATCCATCTCCGTGCTGGGTCCAATAGTTCC | 20 |
| G127A_F | GCACAGAGATGCTTCTGACTGGGAACCATTGTTG | 21 |
| G127A_R | CCCAGTCAGAAGCATCTCTGTGCTGGGTCCAATAG | 22 |
| E175Q_F | ACTTACTAAGCAGTTCGTAGGTGGAGTAGGCG | 23 |
| E175Q_R | CTCCACCTACGAACTGCTTAGTAAGTATGCCGTCGAACTC | 24 |
| V177L_F | TAAGGAATTCTTGGGTGGAGTAGGCGCCG | 25 |
| V177L_R | CCTACTCCACCCAAGAATTCCTTAGTAAGTATGCCGTCG | 26 |
| V180A_F | CGTAGGTGGAGCTGGCGCCGCCATCGTG | 27 |
| V180A_R | TGGCGGCGCCAGCTCCACCTACGAATTCCTTAGTAAG | 28 |
| G202K_F | TGCTGACATGAAGGGAAGAGTATTTACAAAAATTATGTATTCC | 29 |
| G202K_R | ATACTCTTCCCTTCATGTCAGCAATTTGCACAG | 30 |

TABLE 1-continued

| Name | Sequence | SEQ ID NO. |
|---|---|---|
| N250R_F | AGTCGATTACAGAAGACGTCTGGTGTACGAATCC | 31 |
| N250R_R | CCAGACGTCTTCTGTAATCGACTCGGTTATTAATGATTAGC | 32 |
| D363E_F | GAGATTAATACTAATGAGGTTTATTCTCTTGTTTTGTCCG | 33 |
| D363E_R | CAAGAGAATAAACCTCATTAGTATTAATCTCATGTAGGGAATATAATTTATC | 34 |
| 13MUT_F | CCCTGTGCAAGTAACTAATAAGAAGAAGCAAGTATTTACAAAAATTATGTATTCCGAGG | 35 |
| 13MUT_R | TTGTAAATACTTGCTTCTTCTTATTAGTTACTTGCACAGGGTATACCAAATTAC | 36 |
| P98A_F | GGTTGTCGATGCTACGGTCATAGTAAAGGGAAATAAGTTG | 37 |
| P98A_R | CTATGACCGTAGCATCGACAACCCTTGAAACTG | 38 |
| Y249G_F | CCGAGTCGATGGAAATAGACGTCTGGTGTACGAATC | 39 |
| Y249G_R | GACGTCTATTTCCATCGACTCGGTTATTAATGATTAGC | 40 |

Restriction sites are underlined and mutated nucleotides are given in bold.

1.3 Expression and Purification of Tr6 and Mutants Thereof Expressed in Yeast

Transformation and selection of zeocin resistant *P. pastoris* X-33 strains expressing the Tr6 and mutants thereof was carried out essential as described in [14]. For low-scale protein synthesis, *P. pastoris* X-33 harboring pPICZα with mutated genes were grown in 180 mL BMMY (10 g/L yeast extract, 20 g/L peptone, 100 mM potassium phosphate (pH 6), 13.4 g/L yeast nitrogen base, 0.4 mg/L biotin and 0.5° A) methanol) shaking at 30° C. for three days. Protein synthesis was induced every 24 hours by addition of methanol to a final concentration of 0.5%. Cells were removed by centrifugation for 5 min at 3000 g and supernatant was subsequently sterile filtered using a 0.2 µm Minisart filter (Sartorius AG). The supernatant was concentrated about 100-fold using Vivaspin20 concentrators with a 30 kDa cutoff (Sartorius AG). 6xHis-tagged protein was purified from concentrated samples using Ni-sepharose (GE Healthcare) columns in accordance with manufacturer's instructions, desalted with PD-10 columns (GE Healthcare) into a buffer containing 20 mM sodium phosphate (pH 7.4), 100 mM NaCl and 10° A) glycerol and finally concentrated to about 200 µL using Vivaspin0.5 concentrator with 50 kDa cutoff (Sartorius AG).

For large-scale production, *P. pastoris* X-33 harboring pPICZα with mutated genes were grown in a 5 L Sartorius Biostat Aplus fermentor as described previously [13]. The 6xHis-tagged protein was purified by $Cu^{2+}$ affinity column chromatography using a CIM® IDA-8f ml Tube Monolithic Column (BIA Separations GmbH, Villach, Austria) as described previously [14]. Protein concentrations were determined using the BCA protein assay (Thermo scientific) with bovine serum albumin as standard.

Example 2 Methods for Measuring the Trans-Sialidase and Sialidase Enzymatic Activity 2.1 Trans-Sialidase Activity Assay Trans-sialidase activity was assayed as described previously [17] but with the following modifications. Reactions were performed in 50 mM phosphate-citrate (pH 6) at 30° C. using 2.9 µg/mL enzyme. The assay employed 1 mM cGMP-bound sialic acid as donor substrate and MU-Gal as the acceptor. MU-Gal at 0.5 mM was the highest final concentration to be tested due to its low solubility in aqueous solution. A solution of 87 mM MU-Gal in DMSO was diluted to 2 mM in 50 mM phosphate-citrate buffer (pH 6) immediately before preparing the reactions. When assaying crude enzyme preparations from *P. pastoris*, a background signal was observed, and attributed to cleavage of MU-Gal by endogenous β-galactosidase. This background signal could be removed by washing the column eight times with 440 µL of 5 mM HCl after sample application without desorption of the sialylated product and this was therefore done routinely.

2.2 Sialidase Activity Assays

Sialidase activity was measured in a reaction containing 50 mM phosphate-citrate buffer (pH 7), 0.75 mM pNP-NeuAc and 3 µg/mL sialidase enzyme. Reactions were initiated by addition of substrate and followed spectrophotometrically at 410 nm at 30° C. pH 7 was chosen to enable detection of released pNP in a continuous assay. Reaction rates were normalized as ° A) of the activity of the Tr6 parent enzyme. For measurement of hydrolysis of natural substrates, the assay was performed with either 1 mM 3'-sialyllactose, 1 mM 6'-sialyllactose or 1 mM cGMP-bound sialic acid in 50 mM phosphate-citrate buffer (pH 5) using 1 µg/mL enzyme. Reactions were started by addition of enzyme and stopped by adding $H_2SO_4$ to 45 mM final concentration. Quantification of free sialic acid was performed using a 2-thiobarbituric acid assay [15] with the modification that butanol extraction was substituted with mixing with dimethyl sulfoxide (DMSO) [16].

Figure 3:
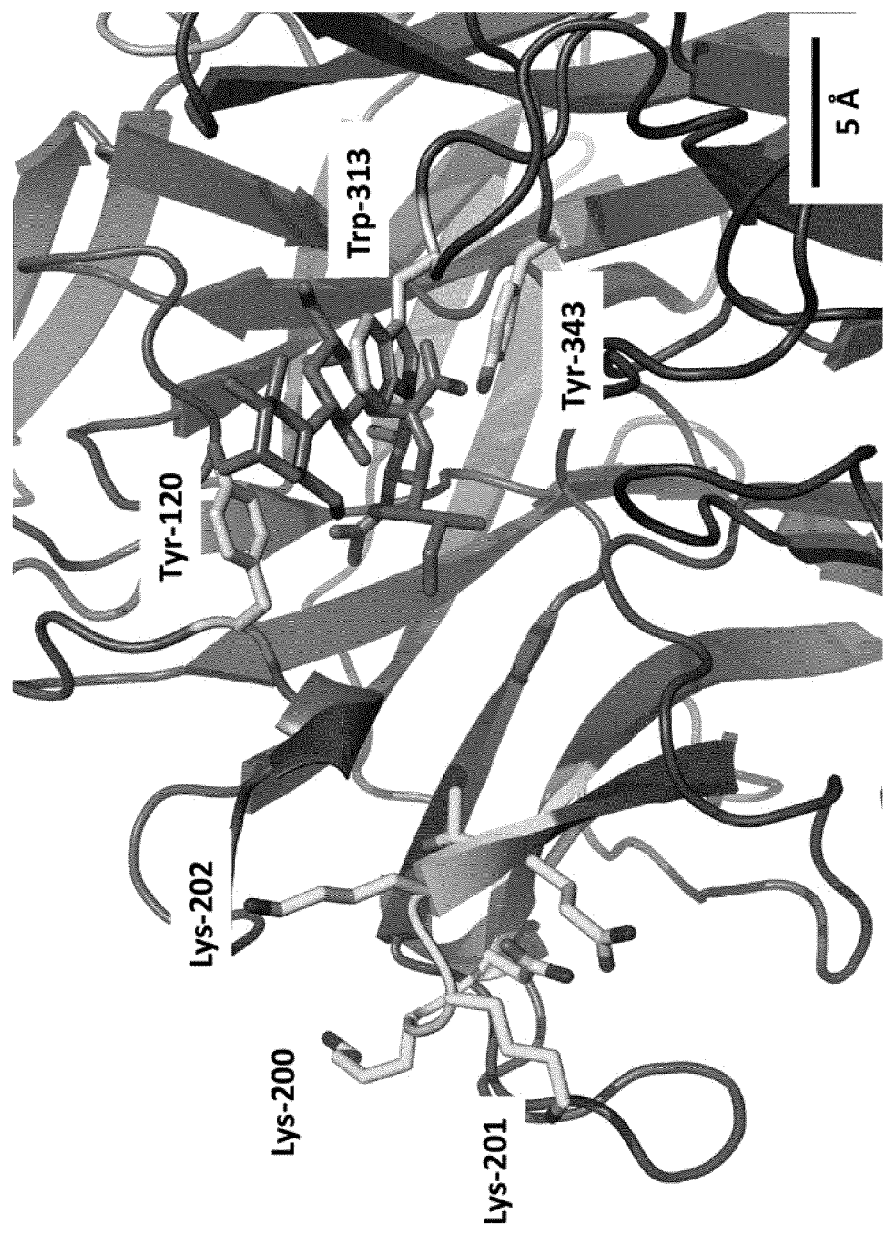
FIG. 3. Homology model of Tr13 (mutant trans-sialidase of the invention). Close-up of the active site with a sialyllactose docked (dark gray). Acceptor binding site residues Tyr-120 and Trp-313 and catalytic nucleophile Tyr-343 side chains are shown in gray. The seven introduced amino acids are shown in light gray.
Figure 4:
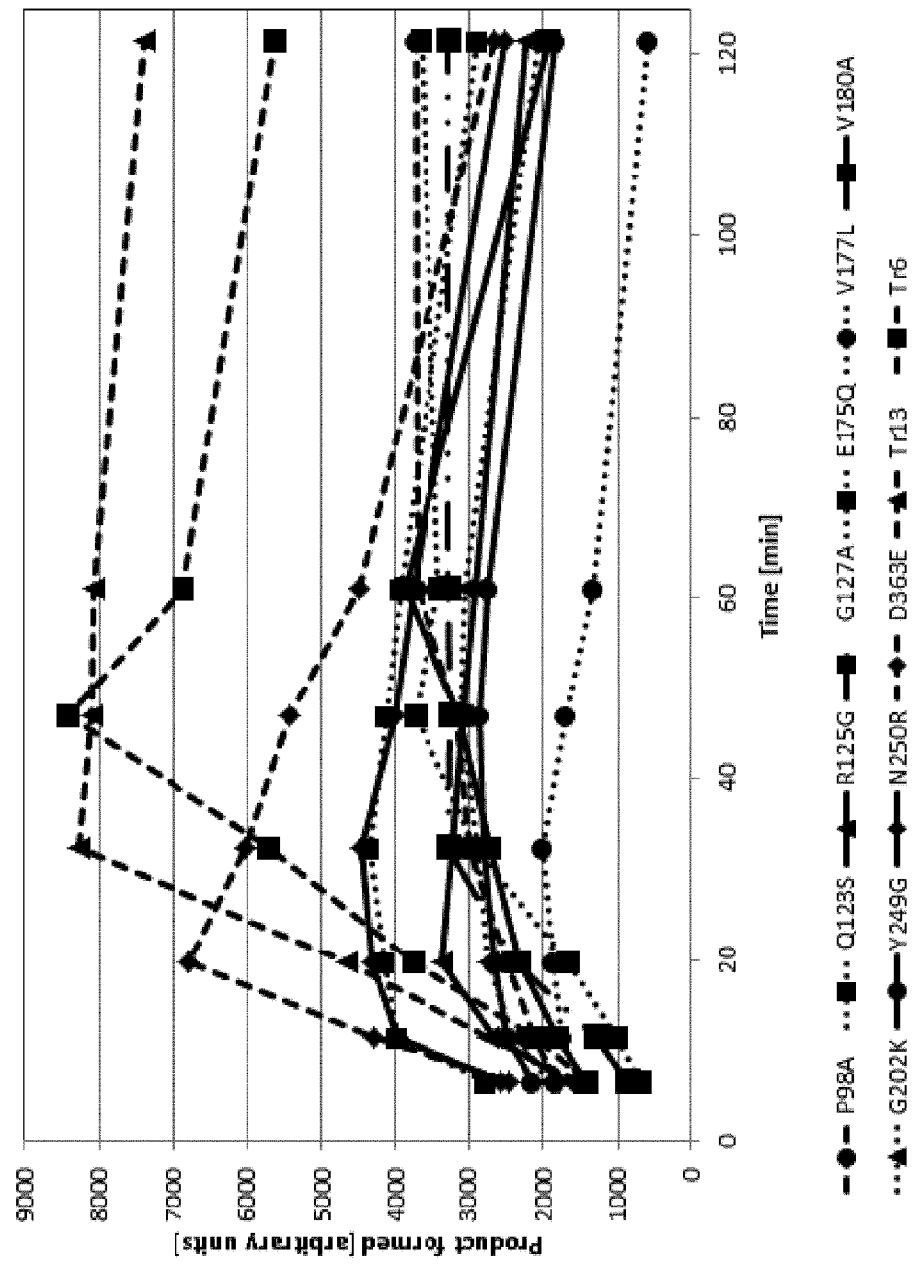
FIG. 4. Trans-sialidase activity of Tr6 and derived mutants using cGMP as sialic acid donor and methylumbelliferyl-pyrogalactoside as acceptor. Product formation is shown in arbitrary units.
Figure 5:
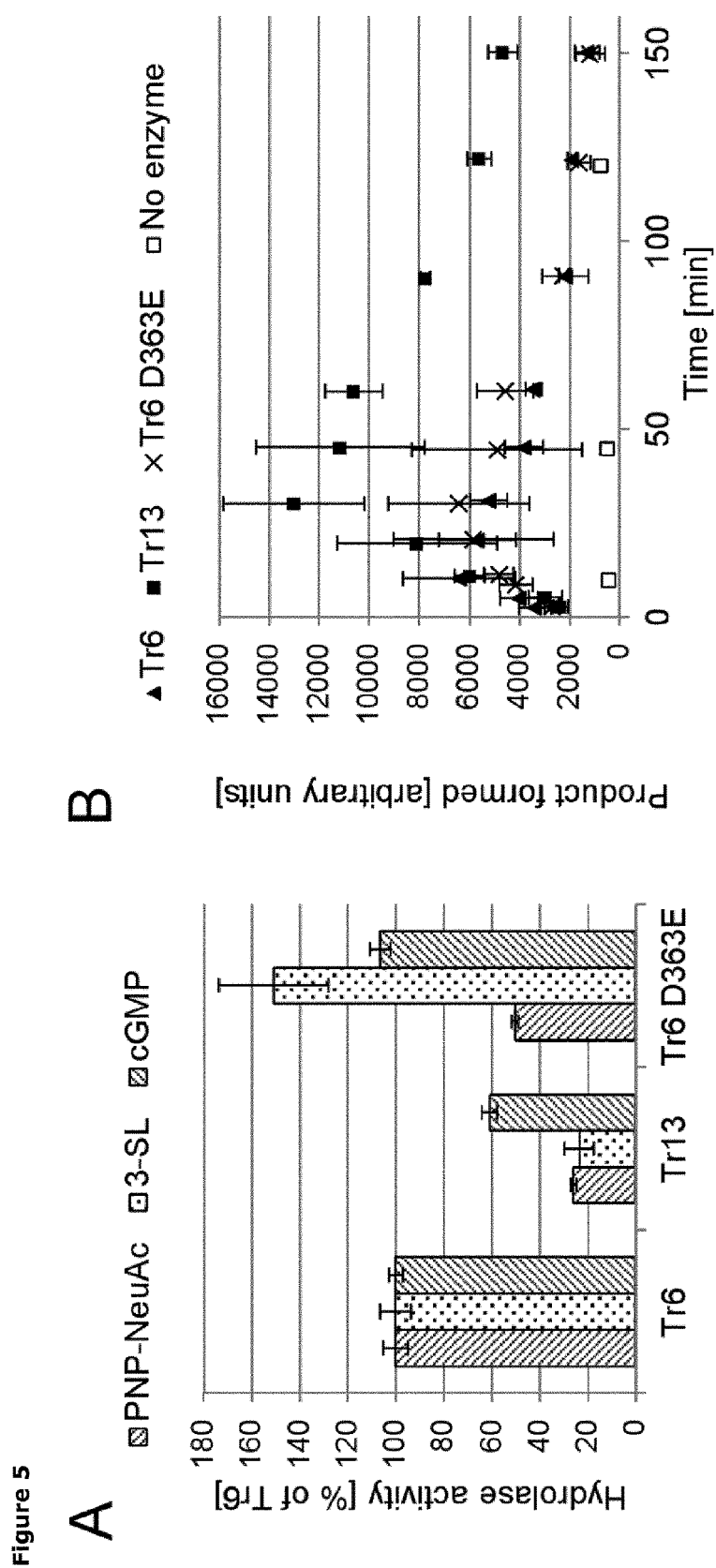
FIG. 5. Enzyme activity of Tr6 and selected mutants Tr13 and Tr6 D363E. A) Hydrolase activity on the substrates pNP-Neu5Ac, 3'-sialyllactose, and cGMP. B) Trans-sialidase activity using cGMP as sialic acid donor and MU-gal as acceptor.

Example 3 a Positively-Charged Motif on the Border of the Binding Cleft of Sialidase Quenches its Hydrolytic Activity 3.1 Selection of Candidate Residues in Tr6 Sialidase for Mutation Screening The catalytic domains of the sialidases were identified using NCBI Conserved Domain Search [10]. Pymol v1.3 (Schrödinger) was used to identify amino acids within 14 Å of the sialic acid binding site. The *T. rangeli* sialidase mutant Tr6 (see below) and trans-sialidases from *T. cruzi* (TcTS) (Uniprot ID Q26966), *Trypanosoma congolense* (Uniprot ID G0WJG3) and *Trypanosoma brucei* (Uniprot ID Q57XJ2) were aligned using ClustalW [11] (FIG. 2). Ranking of chemical difference between substituted amino acids in Tr6 vs. TcTS was done based on being first- or second sphere relative to the substrate and based on the polar/nonpolar and small/large distinction; such property-based selection turned out to correlate well with standard substitution matrices (BLOSUM62), i.e. the most unlikely substitutions were considered noteworthy. A 3D-model of one mutant, Tr13, was made using HHpred [12] with automatic template selection (1ms9_A) (FIG. 3). The Tyr120 side chain conformation was manually changed to resemble that of the solved structure (PDB 1WCS). A comparison of the amino acid sequence of *T. cruzi* trans-sialidase (TcTS) and *T. rangeli* sialidase (TrSA), in particular those residues lying within 14 Å of the sialic acid binding site, reveal a large number of candidate amino acid residues whose substitution might account for the former's trans-sialidase activity. The candidate amino acids were evaluated in terms of their impact on degree of surface exposure, hydrogen bonding, extent of change in chemical structure/properties, and their distance from the acceptor binding site. On this basis, the single residues or a combination of residues depicted in the primary sequence of the catalytic domain shown in FIG. 2 were selected for mutagenesis.

3.2 Measurement of Net Trans-Sialylated Product Yield by Tr6 Sialidase Mutants

To assess the performance of the mutant enzymes, they were produced by recombinant expression in *P. pastoris*, transformed with the respective mutant gene, by growth in shake flask cultures. The trans-sialidase activity of the expressed mutant enzymes was measured with a fluorescence-based assay using cGMP as sialic acid donor and methylumbelliferyl-β-D-galactopyranoside (MU-Gal) as acceptor (FIG. 4). As the detected product is a measure of both the trans-sialidase activity (product formation) and hydrolase activity (product degradation) the assay provides an effective screen for mutants having a higher trans-sialidase to hydrolase activity ratio.

3.3 Selected Tr6 Sialidase Mutants Catalyze a Net Increase in Trans-Sialydated Product Yield All the Tr6 sialidase mutants were shown to be active enzymes (FIG. 4). Reversion of two of the mutations (P98A and Y249G) originally introduced in the Tr6 parent sialidase, led to a reduction in trans-sialidase activity over the Tr6 parent. This confirms that these two residues in Tr6 (P98 and Y249) contribute to trans-sialidase activity of this enzyme. Of all mutants tested, only two mutants, namely Tr13 (comprising a VTNKKKQ (SEQ ID NO.: 58) motif) and Tr6 D363E enhanced trans-sialidase activity relative to Tr6, while all other mutants displayed a decreased trans-sialidase activity. When the Tr6 parent sialidase was mutated by a single amino acid substitution to create a +1 net charge for residues 197-303 (IADMKGR (SEQ ID NO.: 63)) this led to a significant loss of activity, compared to the Tr6 parent. The net +3 charge of the corresponding motif in the Tr13 mutant thus appears to provide a significant and unexpected improvement in trans-sialidase activity relative to Tr6. The parent enzyme Tr6 and the two mutants Tr13 and Tr6 D363E were produced in a 5 L fermentor and purified in amounts sufficient to characterize their catalytic properties. Hydrolase activity was measured using the artificial substrate para-nitrophenyl neuraminic acid (pNP-NeuSAc) as well as the natural substrates 3'-sialyllactose, 6'-sialyllactose and cGMP. The a-2,6-linked sialic acid constitutes about 50% of total sialic acid content in cGMP [21]. Since none of the enzymes exhibited detectable activity on 6'-sialyllactose (data not shown), it was unlikely that a-2,6-linked sialic acid in cGMP can be used as a donor.

Tr13 showed greatly reduced hydrolase activity for all 3 substrates, while D363E only showed reduced hydrolase activity on pNP-Neu5Ac (FIG. 5A).

In the trans-sialidase activity time course assay, the initially measured product formation represents the trans-sialidase reaction rate, while maximum product formation is a measure of both trans-sialidase activity (product formation) and hydrolase activity (product degradation). While, Tr6 and Tr13 appeared to have similar trans-sialidase activity, Tr13 gave twice the trans-sialylated product yield, under these reaction conditions (FIG. 5B), confirming the reduced hydrolytic activity of this Tr13 mutant trans-sialidase. By contrast, the Tr6 D363E had a similarly low product formation profile as Tr6, consistent with their similar hydrolytic activity using cGMP as donor (FIG. 5A).

The Tr13 mutant, comprising a VTNKKKQ (SEQ ID NO.: 58) motif, introduces three lysine residues, where K200 and K201 are partly shielded from the active site (FIG. 3) while K202 points towards the center of the active site. Introduction of the single mutation G202K, which is part of the VTNKKKQ (SEQ ID NO.: 58) motif, does not confer the same properties since this mutant exhibited reduced trans-sialidase activity compared to the parent. The improved maximal yield obtained with the Tr13 mutant suggests that the VTNKKKQ (SEQ ID NO.: 58) motif does not affect acceptor binding affinity but rather uniquely reduces the hydrolytic activity (water kcat and/or KM).

The mechanism by which the VTNKKKQ (SEQ ID NO.: 58) motif exerts its effect is hypothesized to involve impairing water nucleophilicity for attack on sialic acid (by partial disruption of the water network) and by reducing water's retention time in the active site in competition with the acceptor. The effect may be acceptor-dependent, as the total extend of hydrolysis not only depends on the impaired water network but also the KM of the acceptor during trans-sialylation, which affects acceptor vs. water retention time and thus, the competition between hydrolysis and trans-sialylation.

Thus the Tr13 mutant trans-sialidase represents a major advance in engineering a hydrolysis-impaired sialidase enzyme. The insertion of the VTNKKKQ (SEQ ID NO.: 58) motif is sufficient to confer low hydrolase activity, approaching the very low levels of hydrolase activity characteristic of TcTS to a sialidase enzyme. TcTS is distinguished by both an exceptionally low hydrolase activity and the higher affinity for lactose in TcTS compared to Tr6. Within protein engineering at large, viable mutants with improved properties that deviate so substantially from a wild type (by 13 site changes including a 7 amino acid loop structure with a +3 charge difference) are unusual (if not unprecedented).

Example 4 Optimal Reaction Conditions and Specific Activity of Tr13 Mutant Trans-Sialidase Catalyzed Trans-Sialylation 4.1 Optimized Reactions Conditions for Tr13 Mutant Trans-Sialidase Optimal reaction conditions (pH, temperature, and concentration of donor and acceptor) were determined employing a quadratic central composite design. MODDE Version 7.0.0.1 (Umetrics AB, Umeå, Sweden) was used as a tool to design the experimental frame and to fit and analyze the data by multiple linear regression analysis. The pH regimes 3, 4 and 5, the incubation temperatures 20, 40 and 60° C. and the concentrations of the acceptor lactose of 117, 234 and 351 mM were tested. Reactions used a fixed concentration of cGMP-bound sialic acid of 8 mM in 15 mM phosphate-citrate buffer with specified pH values using 15 µg/mL Tr13. Lactose and cGMP were solubilized in buffer and pre-incubated at specific temperatures, before the reactions were initiated by addition of enzyme. The biocatalysis process was allowed to proceed for 20 min before the reaction was stopped by heating for 10 min at 90° C. Concentration of sialyllactose was determined by HPAEC, as described in 4.2.

The best reaction conditions were identified at 351 mM lactose (highest tested), pH 3 (lowest tested) and at 20° C. (lowest tested) using 8 mM cGMP (data not shown).

4.2 Quantification of Sialyllactose

Sialyllactose was quantified by High-performance anion exchange chromatography (HPAEC-PAD) using a Dionex BioLC system consisting of GS50 gradient pumps, ED50 electrochemical detector, AS50 chromatography compartment coupled to an AS50 autosampler (Dionex Corp., Sunnyvale, Calif.). Samples (10 µL) were injected on a CarboPac™ PA1 (4 mm×250 mm) analytical column (Dionex Corp., Sunnyvale, Calif.) at a flow rate of 1 mL/min. The elution program was based on the method described in [18] except for the modifications in the eluent system given below. The eluent system comprised of deionised water (A), 0.5 M NaOH (B), 1 M NaOAc (C). For the first 3 min an isocratic elution of 80:20 (% A:B) was applied, which was followed by a linear gradient from 80:20 (% A:B) to 60:20:20 (% A:B:C) from 3 to 27 min. Strongly retained anions were removed from the column by isocratic elution at 40:20:40 (% A:B:C) from 27 to 31 min. Subsequently the column was re-equilibrated for 7 min with 80:20 (% A:B).

4.3 Specific Activity of Tr13 Mutant Sialidase Catalyzed Trans-Sialylation

Figure 6:
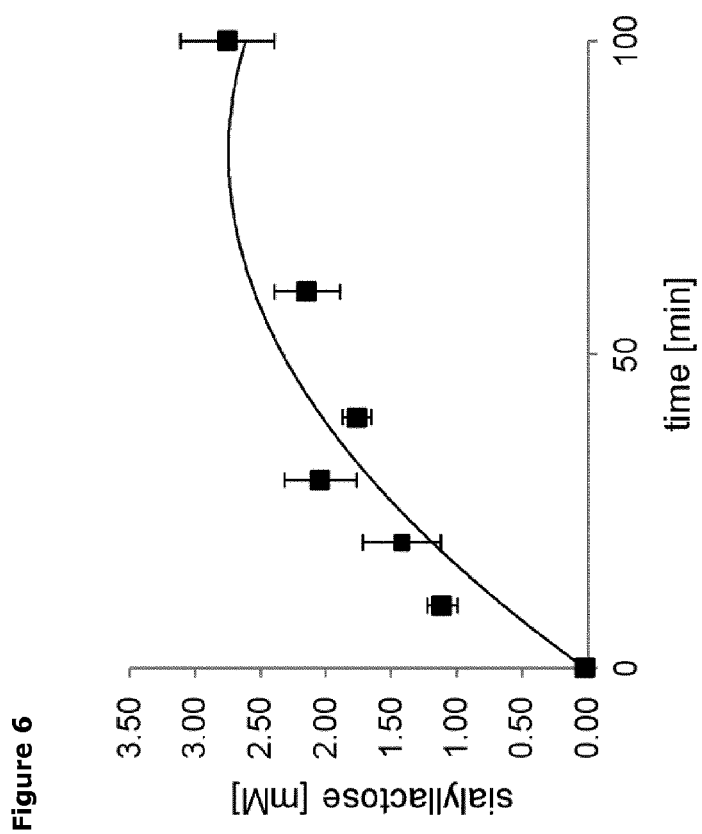
FIG. 6. Time course of trans-sialylation catalysed by Tr13. Accumulation of 3'-sialyllactose over time at 25° C., pH 3, 351 mM lactose and 8 mM cGMP-bound sialic acid.

A time study was performed at these conditions and the specific trans-sialidase activity of the enzyme was determined (FIG. 6). The reaction was followed by sampling in a 100 min period and concentration of sialyllactose was determined by LC/MS as described in Example 5. The samples at $t=0_{min}$ were made using heat-inactivated enzyme. Three replicates were made and each data series fitted to a second order polynomial function. The slope to $t=0_{min}$ for each series was used to calculate the specific activity and the standard deviation.

The specific trans-sialidase activity measured as number of sialyl-moieties transferred of Tr13 was 4.4+/−0.7 nmol*min$^{-1}$ per µg of enzyme on cGMP. It was apparent that a higher product yield could be obtained by extending the reaction time from 20 up to 100 minutes with no detectable product degradation, since no free sialic acid was detected by LC/MS. A maximum yield (not determined) of at least about 2.5 mM 3'-sialyllactose is predicted by extrapolation. In cGMP, sialic acid is bound as α-2,3-sialic acid and α-2,6-bound sialic acid in a ratio of about 1:1 [21] and hence only 4 of the 8 mM cGMP-bound sialic acid was theoretically accessible giving a yield of about 63%.

Example 5 Tr13 Catalyzed Production and Purification of Sialylated Glycans

The ability of Tr13 to trans-sialylate different glycan acceptor molecules (GOS, IMO, lactulose, melibiose, maltose, and fucose) was tested as follows. The reactions were carried out in stirred glass bottles in reaction volumes of 50 mL for melibiose and maltose, 88 mL for fucose, 100 mL for lactulose, and 250 mL for GOS and IMO. The reaction was performed in 15 mM phosphate-citrate buffer (pH 3) with 351 mM sialic acid acceptor (GOS, IMO, lactulose, melibiose, maltose and fucose) and 8 mM cGMP-bound sialic acid at 25° C. using 15 µg/mL enzyme. Prior to the reaction, the substrates were pre-incubated in the buffer. The reaction was carried out for 20 minutes and then stopped by enzyme inactivation by heating at 90° C. for 10 minutes.

5.1 Separation of Trans-Sialylation Products

The reaction mixture was then applied to a HiScale 50/20 (GE Healthcare) anion exchange chromatography column packed with 402 mL of Sepharose Q FF. The separation was done at ambient temperature with an ÄKTA purifier 100 work station equipped with a P-900 pump, UV-900 monitor, and Frac-950 fraction collector, all controlled by UNICORN software (GE Healthcare). The elution was performed at a flow rate of 70 mL/min and monitored at 210 nm. Before injection, the column was equilibrated with 5 column volumes (CV) of water. After injection the column was washed with 3 CV of water which elutes neutral, unreacted acceptor molecules. Negatively charged compounds, i.e. sialylated products and afterwards free sialic acid, and then eluted with 3.5 CV of 40 mM ammonium formate. The column is then flushed clean with 2 CV of 400 mM ammonium formate, and then regenerated with 3 CV of water. Fractions of interest were collected automatically. The products were lyophilized and ammonium formate was removed by repeated solubilization and lyophilization. Product structures were determined by LC/MS, as described below. According to LC/MS analysis, the anion exchange step completely separated the sialylated compounds from both sialic acid, and from the acceptor used in the reaction (see FIG. 7).

5.2 Identification of Trans-Sialylation Products by Capillary Liquid Chromatography/Mass Spectrometry (LC/MS)

LC/MS analyses were performed on an Agilent 1100 LC/Agilent 6340 ion trap MS system was used. Oligosaccharides were separated using a Hypercarb porous graphitic carbon (PGC) column (0.32×150 mm, 5 µm, Thermo scientific) at 30° C. Samples (0.5 µL) were loaded onto the column in 10 mM ammonium bicarbonate. Gradient elution was achieved using a binary solvent system consisting of (A) 10 mM ammonium bicarbonate, adjusted to pH 8.5 with ammonium hydroxide, and (B) 100% acetonitrile at a flow rate of 5 µL/min. The gradient was initially at 98:2 (% A:B) for 5 min, followed by a linear increase to 42:58 (% A:B) at 33 min. This concentration of B was held for 3 min. Subsequently the eluent was returned to 98:2 (% A:B) at 40 min and the system was allowed to equilibrate for 10 min prior to the next injection. All solvents used were of the highest HPLC grade. A PEEK™ Tubing (30 cm×65 µm ID, IDEX Health & Science) was used as transfer line to the electrospray ion source of the MS system. The mass spectrometry was performed in negative ion mode, and was scanned in the range m/z 150-2200 (2 microscans, maximum accumulation time of 150 ms, an ion current count of 200,000) followed by data-dependent MS2 scans of the four most abundant ions in each MS1 scan.

Figure 7:
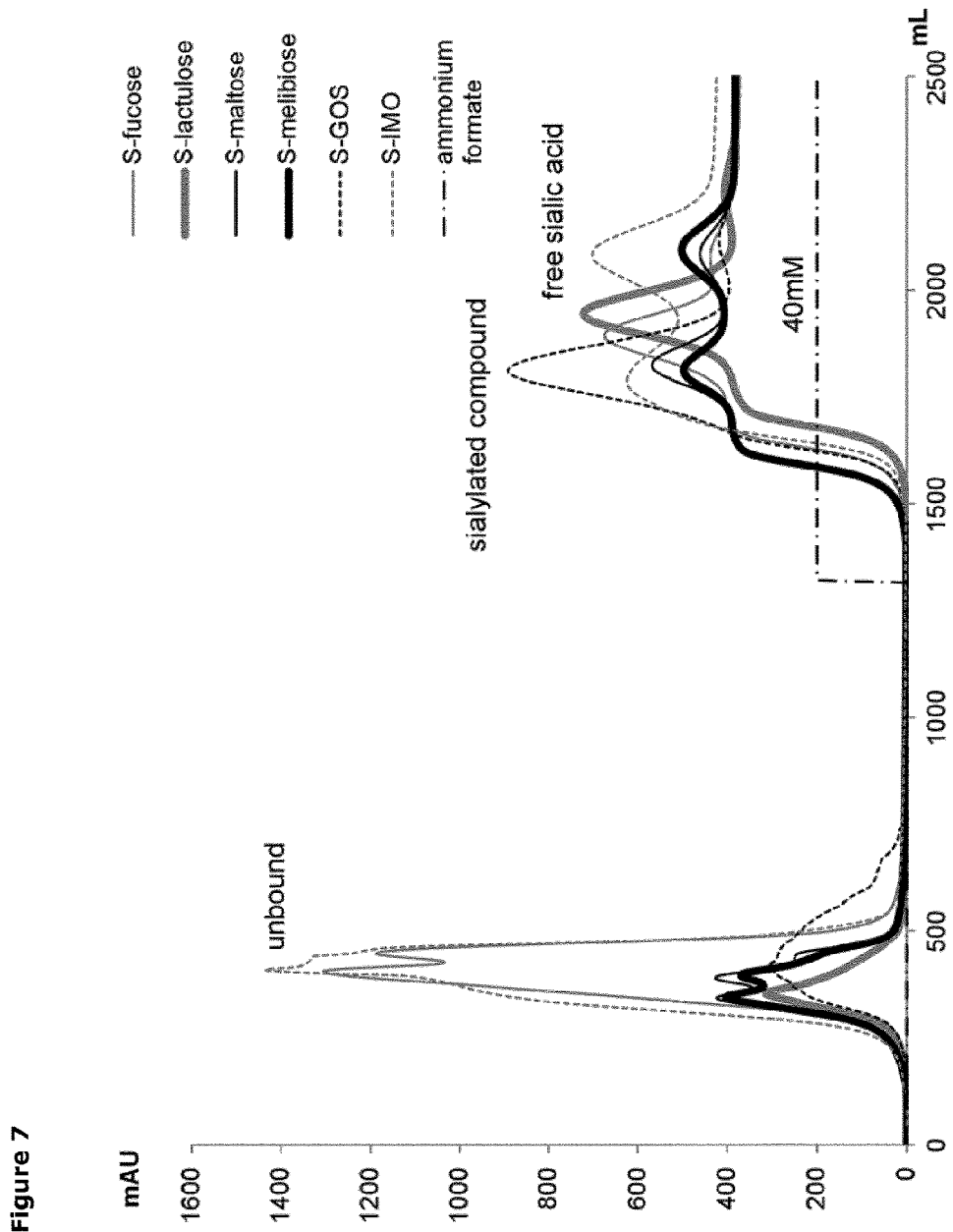
FIG. 7. Anion exchange separation profiles for sialylated glycans catalyzed by Tr13. Sialylated glycans separated from sialic acid and unused acceptor separated on Sepharose Q and detected at 210 nm.

All glycan substrates were shown to the trans-sialylated by Tr13 (FIG. 7). The composition of GOS and IMO sialylation products generated by Tr13 was complex (Table 2). Four and five different sialylated compounds, respectively, were obtained. In the case of GOS, the product of the lowest molecular weight was sialyllactose (m/z of 632), whereas incubation of IMO with cGMP led also to production of sialylated glucose (m/z of 470), since the starting material was abundant in that monomer.

TABLE 2

Products of sialylation of various glycans analysed by LC/MS.

| Acceptor | m/z [M − H]⁻ | Product | Product conc. [g/L] | Product yield [w$_{prod}$/w$_{accep}$] | [mM] |
|---|---|---|---|---|---|
| GOS | 632 | SA-α-Gal-1,4-β-Glc | 1.0 | 0.44% | ND |
|  | 794 | SA-α-Gal-1,4-β-Gal-1,4-β-Glc |  |  |  |
|  | 956 | SA-α-Gal-1,4-β-Gal-1,4-β-Gal-1,4-β-Glc |  |  |  |
|  | 1118 | SA-α-Gal-1,4-β-Gal-1,4-β-Gal-1,4-β-Gal-1,4-β-Glc |  |  |  |
| Fucose | 454 | SA-α-Fuc | 0.66 | 1.17% | 1.46 |
| Melibiose | 632 | SA-α-Gal-1,6-α-Glc | 0.62 | 0.52% | 0.98 |
| Lactulose | 632 | SA-α-Gal-1,4-β-Fru | 1.2 | 0.97% | 1.84 |
| Maltose | 632 | SA-α-Glc-1,4-α-Glc | 0.66 | 0.55% | 1.04 |
| IMO | 470 | SA-α-Glc | 0.72 | 0.60% | ND |
|  | 632 | SA-α-Glc-α-Glc |  |  |  |
|  | 794 | SA-α-Glc-α-Glc-α-Glc |  |  |  |
|  | 956 | SA-α-Glc-α-Glc-α-Glc-α-Glc |  |  |  |
|  | 1118 | SA-α-Glc-α-Glc-α-Glc-α-Glc-α-Glc |  |  |  |

Yields are given as product concentration and as % (w/w) of product produced from acceptor used. ND; the molar concentration of sialylated GOS and IMO could not be calculated since the distribution of different chain lengths was not determined.

Of the compounds produced, sialyllactulose was produced in the highest molar yield. Galactose and the 1,4-β bond between galactose and fructose in lactulose may be a structure that is particularly accessible to the active site cleft of Tr13. Although the acceptors, melibiose (1,6-α-bound galactose) and maltose (1,4-α-bound glucose) are of similar size, their sialylation yield was more than 40% lower.

Example 6 Prebiotic Effect of Various Sialylated Glycans

6.1 Methods for Measuring Bacterial Growth on Sialylated Glycans

Bacterial growth assays on sialylated glycans were performed with the following strains: *Bifidobacterium longum longum* (Danisco Global Culture Collection DGCC 232), *Bifidobacterium longum infantis* (DGCC 233), *Bifidobacterium longum infantis* (DGCC 1497), *Bifidobacterium longum infantis* (DGCC 2238), *Lactobacillus acidophilus* (NCFM, ATCC 700396), *Bifidobacterium longum* (BI-05, DGCC 9917), *Bifidobacterium lactis* (HN019, DGCC2013), and *Clostridium perfringens* (ATCC 13124). The tested sialylated substrates were dissolved in water at 10% (w/v) and sterilized by sterile filtration (0.2 μm Minisart, Sartorius AG, Göttingen, Germany). Galactan from potato (Megazyme International LTD, Bray, Co. Wicklow, Ireland), used as prebiotic standard control, was sterilised by UV-radiation for 30 seconds, due to its high viscosity. The bacterial strains were precultured in MRS-medium (de Man, Rogosa and Sharpe medium without glucose) with no additional sugars added, for 24 h at 37° C. under anaerobic conditions, before being diluted with fresh MRS-medium to 1% (v/v). Growth on test substrates was performed by adding 20 μL of 10% test substrates solutions and 180 μL 1% cell suspension in multi-well plates and growth was followed by measurement of optical density at 600 nm (OD600) using Biolink® software (Labsystems) in a Bioscreen® C system (Labsystems, Helsinki, Finland) as described previously [19]. The growth in MRS-medium without addition of carbohydrates was used as control. The experiments were performed in three replicates for each strain and carbohydrate substrate and growth was determined as the area under the growth curve. Data are given as mean values±standard error.

To assess the impact of sialylation it would have been relevant to compare bacterial growth on sialylated and unsialylated acceptor molecules. Since the distribution of sialylated molecules of different chain length in case of GOS and IMO was not quantified, galactan from potato was used as a control, due to its confirmed prebiotic properties [26].

6.2 the Effect of Tr13 Trans-Sialyated Glycans on Bacterial Growth

All the *B. longum* subsp. *infantis* strains tested contain a sialidase (a prerequisite for utilising the sialylated compounds) as well as *C. perfringens* that contains the necessary enzymes for metabolising sialic acid [27]. Although variations in growth were seen on the different substrates, even within species, it was evident that most bacteria to some extent were able to grow on the sialylated compounds.

As shown in Table 3, sialylated melibiose and maltose did not appear to promote growth of the group of probiotic strains. Growth of *B. infantis* 233, *B. infantis* 1497, and *B. longum* 232, was promoted to various degrees by different sialylated compounds, while sialylated fucose promoted growth of all three. However, none of the sialylated compounds promoted growth of *B. infantis* 2238, *B. lactis, L. acidophilus*, and *B. longum* 9917, while *L. acidophilus* grew well on the prebiotic control substrate galactan. *C. perfringens* grew significantly better than all the probiotic strains on the tested sialylated compounds. Mixed cultures are more likely to reveal a selective growth effect of sialylated on probiotic bacteria.

TABLE 3

Bacterial growth on sialylated glycans.

| | Area under the growth curve [OD$_{600}$ × min]* | | | | | | | |
|---|---|---|---|---|---|---|---|---|
| Bacterial strain | MRS- | S-GOS | S-fucose | S-melibiose | S-lactulose | S-maltose | S-IMO | galactan |
| *B. infantis* 233 | 30 ± 14 | 132 ± 5 | 71 ± 6 | 14 ± 6 | 109 ± 20 | 30 ± 4 | 95 ± 23 | 55 ± 7 |
| *B. infantis* 2238 | 294 ± 68 | 274 ± 18 | 285 ± 15 | 302 ± 2 | 269 ± 20 | 158 ± 24 | 269 ± 6 | 264 ± 7 |
| *B. infantis* 1497 | 31 ± 10 | 42 ± 13 | 149 ± 2 | ND | 34 ± 2 | ND | 45 ± 1 | 40 ± 9 |
| *B. longum* 232 | 79 ± 20 | 162 ± 9 | 192 ± 20 | 104 ± 17 | 134 ± 19 | 122 ± 31 | 107 ± 19 | 42 ± 13 |
| *B. lactis* | 139 ± 70 | 176 ± 18 | 192 ± 27 | ND | 122 ± 18 | 102 ± 8 | 175 ± 13 | 143 ± 15 |

TABLE 3-continued

Bacterial growth on sialylated glycans.

Area under the growth curve [OD$_{600}$ × min]*

| Bacterial strain | MRS- | S-GOS | S-fucose | S-melibiose | S-lactulose | S-maltose | S-IMO | galactan |
|---|---|---|---|---|---|---|---|---|
| L. acidophilus | 180 ± 28 | 159 ± 4 | 188 ± 18 | 192 ± 4 | 128 ± 2 | 193 ± 12 | 217 ± 19 | 371 ± 10 |
| B. longum 9917 | 106 ± 30 | 71 ± 5 | 114 ± 15 | 70 ± 8 | 34 ± 14 | 101 ± 6 | 103 ± 9 | 93 ± 44 |
| C. perfringens | 455 ± 32 | 722 ± 52 | 811 ± 48 | ND | 541 ± 17 | 844 ± 99 | 1098 ± 61 | 447 ± 46 |

*Area under the growth curve of probiotic strains and pathogenic Clostridium perfringens grown on sialylated glycans; galactan was used as a control; growth responses for the substrates are shown for a substrate concentration of 10 g/L for all bacterial strains. Data are given as average values of 3 replicates and shown ± s.d. The growth of B. longum infantis 1497, B. lactis and C. perfringens was not tested on sialylmelibiose, nor was growth of B. longum infantis 1497 on sialylmaltose (ND).

Recently, three fucosylated HMOs were shown to stimulate bifidobacteria, while E. coli and C. perfringens were unable to utilise the HMOs [28], and the organic acid fermentation products inhibited their growth. Furthermore, a primary functionality of sialylated HMOs is rather attributed to their role as decoy molecules and in modulation of the immune system.

REFERENCES

1. Chen X, Varki A (2010) Advances in the biology and chemistry of sialic acids. ACS Chem Biol 5: 163-176.
2. Singh S, Scigelova M, Hallberg M L, Howarth O W, Schenkman S, et al. (2000) Synthesis of sialyloligosaccharides using the trans-sialidase from Trypanosoma cruzi: novel branched and di-sialylated products from digalactoside acceptors. Chem Commun 1013-1014.
3. Pereira M E, Zhang K, Gong Y, Herrera E M, Ming M (1996) Invasive phenotype of Trypanosoma cruzi restricted to a population expressing trans-sialidase. Infect Immun 64: 3884-3892.
4. Paris G, Ratier L, Amaya M F, Nguyen T, Alzari P M, et al. (2005) A Sialidase Mutant Displaying trans-Sialidase Activity. 3 Mol Biol 345: 923-934.
5. Amaya M F, Watts A G, Damager I, Wehenkel A, Nguyen T, et al. (2004) Structural insights into the catalytic mechanism of Trypanosoma cruzi trans-sialidase. Structure 12: 775-784.
6. Damager I, Buchini S, Amaya M F, Buschiazzo A, Alzari P, et al. (2008) Kinetic and mechanistic analysis of Trypanosoma cruzi trans-sialidase reveals a classical ping-pong mechanism with acid/base catalysis. Biochemistry 47: 3507-3512.
7. Buschiazzo A, Amaya M F, Cremona M L, Frasch A C, Alzari P M (2002) The crystal structure and mode of action of trans-sialidase, a key enzyme in Trypanosoma cruzi pathogenesis. Mol Cell 10: 757-768.
8. Buschiazzo A, Tavares G A, Campetella O, Spinelli S, Cremona M L, et al. (2000) Structural basis of sialyltransferase activity in trypanosomal sialidases. EMBO J 19: 16-24.
9. Paris G, Cremona M L, Amaya M F, Buschiazzo A, Giambiagi S, et al. (2001) Probing molecular function of trypanosomal sialidases: single point mutations can change substrate specificity and increase hydrolytic activity. Glycobiology 11: 305-311.
10. Marchler-Bauer A, Lu S, Anderson J B, Chitsaz F, Derbyshire M K, et al. (2011) CDD: a Conserved Domain Database for the functional annotation of proteins. Nucleic Acids Res 39: D225-D229.
11. Larkin M A, Blackshields G, Brown N P, Chenna R, McGettigan P A, et al. (2007) ClustalW and ClustalX version 2. Bioinformatics 23: 2947-2948.
12. Söding J, Biegert A, Lupas A N (2005) The HHpred interactive server for protein homology detection and structure prediction. Nucleic Acids Res 33: W244-W248.
13. Michalak M, Thomassen L V, Roytio H, Ouwehand A C, Meyer A S, et al. (2012) Expression and characterization of an endo-1,4-β-galactanase from Emericella nidulans in Pichia pastoris for enzymatic design of potentially prebiotic oligosaccharides from potato galactans. Enzyme Microbl Technol 50: 121-129.
14. Silva I R, Larsen D M, Meyer A S, Mikkelsen J D (2011) Identification, expression, and characterization of a novel bacterial RGI Lyase enzyme for the production of biofunctional fibers. Enzyme Microb Technol 49: 160-166.
15. Denny P C, Denny P A, Allerton S E (1983) Determination of sialic acid using 2-thiobarbituric acid in the absence of hazardous sodium arsenite. Clin Chim Acta 131: 333-336.
16. Skoza L, Mohos S (1976) Stable thiobarbituric acid chromophore with dimethyl sulphoxide. Application to sialic acid assay in analytical de-O-acetylation. Biochem J 159: 457-462.
17. Schrader S, Tiralongo E, Paris G, Yoshino T, Schauer R (2003) A nonradioactive 96-well plate assay for screening of trans-sialidase activity. Anal Biochem 322: 139-147.
18. Kunz C, Rudloff S, Hintelmann A, Pohlentz G, Egge H (1996) High-pH anion-exchange chromatography with pulsed amperometric detection and molar response factors of human milk oligosaccharides. J Chromatogr B 685: 211-221.
19. Mäkeläinen H, Saarinen M, Stowell J, Rautonen N, Ouwehand A C (2010) Xylo-oligosaccharides and lactitol promote the growth of Bifidobacterium lactis and Lactobacillus species in pure cultures. Benefic Microb 1: 139-48.
20. Henikoff S, Henikoff J G (1992) Amino acid substitution matrices from protein blocks. Proc Natl Acad Sci USA 89:10915-10919.
21. Saito T, Itoh T (1992) Variations and distributions of O-glycosidically linked sugar chains in bovine κ-casein. 3 Diary Sci 75: 1768-1774.
22. Scudder P, Doom J P, Chuenkova M, Manger I D, Pereira M E A (1993) Enzymatic Characterization of β-D-Galactoside α2,3-trans-Sialidase from Trypanosoma cruzi. 3 Biol Chem 268: 9886-9891.
23. Ribeirão M, Pereira-Chioccola V L, Eichinger D, Rodrigues M M, Schenkman S (1997) Temperature differences for trans-glycosylation and hydrolysis reaction reveal an acceptor binding site in the catalytic mechanism of Trypanosoma cruzi trans-sialidase. Glycobiology 7: 1237-1246.
24. Schenkman S, Jiang M S, Hart G W, Nussenzweig V (1991) A novel cell surface trans-sialidase of Trypano- 25. Schmidt D, Sauerbrei B, Thiem J (2000) Chemoenzymatic Synthesis of Sialyl Oligosaccharides with Sialidases Employing Transglycosylation Methodology. 3 Org Chem 65: 8518-8526.
26. Onumpai C, Kolida S, Bonnin E, Rastall R A (2011) Microbial utilization and selectivity of pectin fractions with various structures. Appl Environ Microbiol 77: 5747-5754.
27. Walters D M, Stirewalt V L, Melville S B (1999) Cloning, Sequence, and Transcriptional Regulation of the Operon Encoding a Putative N-Acetylmannosamine-6-Phosphate Epimerase (nanE) and Sialic Acid Lyase (nanA) in *Clostridium perfringens*. J Bacteriol 181: 4526-4532.
28. Yu Z T, Chen C, Kling D E, Liu B, McCoy J M, et al. (2013) The Principal Fucosylated Oligosaccharides of Human Milk Exhibit Prebiotic Properties on Cultured Infant Microbiota. Glycobiology 23: 169-177.
29. Gaskell A, Crennell S, Taylor G. (1995) The three domains of a bacterial sialidase: a beta-propeller, an immunoglobulin module and a galactose-binding jellyroll. Structure 3:1197-1205.
30. Lamsal B P (2012) Production, health aspects and potential food uses of dairy prebiotic galactooligosaccharides. J Sci Food Agric 92: 2020-2028.
31. Smith L E, Uemura, H, Eichinger D. (1996) Isolation and expression of an open reading frame encoding sialidase from *Trypansoma rangeli* Molecular and Biochemical Parasitology 79: 21-33.
32. Smith L E, Q27064 UniprotKB submitted January 1996 to EMBL/GenBank/DDBJ database.
33. Buschiazzo A, Cremona, M L, Campetella O, Frasch A C C and Sánchez D O. (1993) Sequence of a *Trypansoma rangeli* gene closely related to *Trypansoma cruzi* transsialidase.

The invention claimed is:

1. A mutant polypeptide having at least 80% amino acid sequence identity to amino acid residues 28-372 of SEQ ID NO: 2, and wherein:

a) amino acid residues 197 to 203 of SEQ ID NO: 2 comprise substituted amino acid residues resulting in a net positive charge of at least +3 for residues 197 to 203 of SEQ ID NO: 2, and b) amino acid residues 37, 96, 98, 120, 249, 284 have 100% sequence identity to the corresponding residues in SEQ ID NO: 2, wherein the polypeptide has trans-sialidase activity.

2. The mutant polypeptide of claim 1, wherein the amino acid sequence of residues 197 to 203 in SEQ ID NO: 2 comprises VTNKKKQ.

3. The mutant polypeptide of claim 1, wherein the polypeptide further comprises a C-terminal linker and carbohydrate-binding domain selected from among:

a) C-terminal linker peptide and carbohydrate-binding peptide of *Trypanosoma rangeli* trans-sialidase comprising amino acid residues 373 to 638 of SEQ ID NO: 2;

b) C-terminal linker peptide and carbohydrate-binding peptide of *Trypanosoma cruzi* trans-sialidase comprising SEQ ID NO: 8;

c) C-terminal linker peptide and carbohydrate-binding peptide of *Trypanosoma congolense* trans-sialidase comprising SEQ ID NO: 9; and d) C-terminal linker peptide and carbohydrate-binding peptide of *Trypanosoma brucei* trans-sialidase comprising SEQ ID NO: 10.

4. The mutant polypeptide of claim 1, having an amino acid sequence selected from amino acids residues 28-372; 1-372, 28-638, and 1-638 of SEQ ID NO: 4.

5. The mutant polypeptide of claim 1, wherein the polypeptide is expressed as a fusion protein comprising a homologous or heterologous amino-terminal signal peptide and/or a heterologous peptide having selective substrate binding affinity for purification of the polypeptide.

6. A DNA molecule comprising a positive DNA strand having a nucleic acid sequence encoding the mutant polypeptide of claim 1.

7. A DNA molecule according to claim 6, wherein the nucleotide sequence is selected from among:

a) a nucleotide sequence encoding amino acid residues 28-372 of SEQ ID NO: 4;

b) a nucleotide sequence encoding amino acid residues 1-372 of SEQ ID NO: 4;

c) a nucleotide sequence encoding amino acid residues 28-638 of SEQ ID NO: 4; and d) a nucleotide sequence encoding amino acid residues 1-638 of SEQ ID NO: 4.

8. A recombinant host cell comprising the DNA molecule of claim 6, wherein said cell is prokaryotic or eukaryotic, and is selected from a bacterial cell, a yeast cell and a fungal cell.

9. A method for producing the mutant polypeptide according to claim 1, comprising:

a) providing a recombinant host cell, wherein the cell comprises a DNA molecule, the DNA molecule comprising a nucleic acid sequence encoding the mutant polypeptide according to claim 1, b) incubating the host cell in a medium suitable for expression of the mutant polypeptide, and c) recovering the mutant polypeptide expressed by the host cell in step b) from the medium.

10. An enzyme composition comprising the mutant polypeptide according to claim 1, wherein the composition is formulated as a dry powder, a tablet, or as a liquid.

11. A method for producing sialylated mono- and/or oligo-saccharides, comprising the steps of:

a) providing a sialic acid donor molecule and a molecule comprising an acceptor mono- and/or oligo-saccharide capable of being trans-sialylated;

b) contacting the molecules of (a) with the mutant polypeptide according to claim 1 in an aqueous medium.

12. The method of claim 11, wherein the donor molecule is provided in the form of a dairy side stream, a whey or a casein glycomacropeptide.

13. The method of claim 11, wherein the acceptor glycan is selected from among one or more of galacto-oligosaccharides, fructo-oligosaccharides, malto-oligosaccharides, isomalto-oligosaccharides, lactose, lactosucrose, lactulose, lacto-N-tetraose, lacto-N-neotetraose, lacto-N-fucopentaose I, lacto-N-fucopentaose V, melibiose, maltose, glycosyl sucrose and fucose.

14. The method of claim 13, wherein the acceptor glycan is one or more galacto-oligosaccharide, the method further comprising a preceding step of contacting lactose with a β-trans-galactosidase to produce the one or more galacto-oligosaccharide.

15. A composition comprising sialylated mono- and oligo-saccharides produced by the method according to claim 11, wherein the sialylated oligosaccharides comprise sialylated galacto-oligosaccharides and fructo-oligosaccharides, and wherein said composition is selected from an infant formula, a prebiotic nutritional supplement, and a food supplement.

* * * * *

SEQUENCE LISTING

```
<160> NUMBER OF SEQ ID NOS: 63

<210> SEQ ID NO 1
<211> LENGTH: 641
<212> TYPE: PRT
<213> ORGANISM: Trypanosoma rangeli
<220> FEATURE:
<221> NAME/KEY: PEPTIDE
<222> LOCATION: (1)..(641)
<223> OTHER INFORMATION: T. rangeli mutant sialidase (PBD 1WCS)

<400> SEQUENCE: 1

Ala Ala Ser Leu Ala Pro Gly Ser Ser Arg Val Glu Leu Phe Lys Arg
1               5                   10                  15

Lys Asn Ser Thr Val Pro Phe Glu Glu Ser Asn Gly Thr Ile Arg Glu
                20                  25                  30

Arg Val Val His Ser Phe Arg Ile Pro Thr Ile Val Asn Val Asp Gly
            35                  40                  45

Val Met Val Ala Ile Ala Asp Ala Arg Tyr Glu Thr Ser Phe Asp Asn
        50                  55                  60

Ser Phe Ile Glu Thr Ala Val Lys Tyr Ser Val Asp Asp Gly Ala Thr
65                  70                  75                  80

Trp Asn Thr Gln Ile Ala Ile Lys Asn Ser Arg Ala Ser Ser Val Ser
                85                  90                  95

Arg Val Val Asp Pro Thr Val Ile Val Lys Gly Asn Lys Leu Tyr Ile
                100                 105                 110

Leu Val Gly Ser Phe Asn Lys Thr Arg Asn Tyr Trp Thr Gln His Arg
            115                 120                 125

Asp Gly Ser Asp Trp Glu Pro Leu Leu Val Val Gly Glu Val Thr Lys
        130                 135                 140

Ser Ala Ala Asn Gly Lys Thr Thr Ala Thr Ile Ser Trp Gly Lys Pro
145                 150                 155                 160

Val Ser Leu Lys Pro Leu Phe Pro Ala Glu Phe Asp Gly Ile Leu Thr
                165                 170                 175

Lys Glu Phe Val Gly Gly Val Gly Ala Ala Ile Val Ala Ser Asn Gly
            180                 185                 190

Asn Leu Val Tyr Pro Val Gln Ile Ala Asp Met Gly Gly Arg Val Phe
        195                 200                 205

Thr Lys Ile Met Tyr Ser Glu Asp Asp Gly Asn Thr Trp Lys Phe Ala
        210                 215                 220
```

Glu Gly Arg Ser Lys Phe Gly Cys Ser Glu Pro Ala Val Leu Glu Trp
225                 230                 235                 240

Glu Gly Lys Leu Ile Ile Asn Asn Arg Val Asp Tyr Asn Arg Arg Leu
            245                 250                 255

Val Tyr Glu Ser Ser Asp Met Gly Lys Thr Trp Val Glu Ala Leu Gly
        260                 265                 270

Thr Leu Ser His Val Trp Thr Asn Ser Pro Thr Ser Asn Gln Pro Asp
    275                 280                 285

Cys Gln Ser Ser Phe Val Ala Val Thr Ile Glu Gly Lys Arg Val Met
290                 295                 300

Leu Phe Thr His Pro Leu Asn Leu Lys Gly Arg Trp Met Arg Asp Arg
305                 310                 315                 320

Leu His Leu Trp Met Thr Asp Asn Gln Arg Ile Phe Asp Val Gly Gln
            325                 330                 335

Ile Ser Ile Gly Asp Glu Asn Ser Gly Tyr Ser Ser Val Leu Tyr Lys
        340                 345                 350

Asp Asp Lys Leu Tyr Ser Leu His Glu Ile Asn Thr Asn Asp Val Tyr
    355                 360                 365

Ser Leu Val Phe Val Arg Leu Ile Gly Glu Leu Gln Leu Met Lys Ser
370                 375                 380

Val Val Arg Thr Trp Lys Glu Glu Asp Asn His Leu Ala Ser Ile Cys
385                 390                 395                 400

Thr Pro Val Val Pro Ala Thr Pro Pro Ser Lys Gly Ala Cys Gly Ala
            405                 410                 415

Ala Val Pro Thr Ala Gly Leu Val Gly Phe Leu Ser His Ser Ala Asn
        420                 425                 430

Gly Ser Val Trp Glu Asp Val Tyr Arg Cys Val Asp Ala Asn Val Ala
    435                 440                 445

Asn Ala Glu Arg Val Pro Asn Gly Leu Lys Phe Asn Gly Val Gly Gly
450                 455                 460

Gly Ala Val Trp Pro Val Ala Arg Gln Gly Gln Thr Arg Arg Tyr Gln
465                 470                 475                 480

Phe Ala Asn Tyr Arg Phe Thr Leu Val Ala Thr Val Thr Ile Asp Glu
            485                 490                 495

Leu Pro Lys Gly Thr Ser Pro Leu Leu Gly Ala Gly Leu Glu Gly Pro
        500                 505                 510

Gly Asp Ala Lys Leu Leu Gly Leu Ser Tyr Asp Lys Asn Arg Gln Trp
    515                 520                 525

Arg Pro Leu Tyr Gly Ala Ala Pro Ala Ser Pro Thr Gly Ser Trp Glu
530                 535                 540

Leu His Lys Lys Tyr His Val Val Leu Thr Met Ala Asp Arg Gln Gly
545                 550                 555                 560

Ser Val Tyr Val Asp Gly Gln Pro Leu Ala Gly Ser Gly Asn Thr Val
            565                 570                 575

Val Arg Gly Ala Thr Leu Pro Asp Ile Ser His Phe Tyr Ile Gly Gly
        580                 585                 590

Pro Arg Ser Lys Gly Ala Pro Thr Asp Ser Arg Val Thr Val Thr Asn
    595                 600                 605

Val Val Leu Tyr Asn Arg Arg Leu Asn Ser Ser Glu Ile Arg Thr Leu
610                 615                 620

Phe Leu Ser Gln Asp Met Ile Gly Thr Asp Gly Gly Ala Gly Thr Ala
625                 630                 635                 640

Ala

```
<210> SEQ ID NO 2
<211> LENGTH: 638
<212> TYPE: PRT
<213> ORGANISM: Trypanosoma rangeli
<220> FEATURE:
<221> NAME/KEY: mat_peptide
<222> LOCATION: (1)..(638)
<220> FEATURE:
<221> NAME/KEY: PEPTIDE
<222> LOCATION: (1)..(372)
<223> OTHER INFORMATION: Mutant Tr6 T. rangeli trans-sialiadase -
      N-terminal region and catalytic peptide
<220> FEATURE:
<221> NAME/KEY: PEPTIDE
<222> LOCATION: (28)..(372)
<223> OTHER INFORMATION: Mutant Tr6 T. rangeli trans-sialiadase -
      catalytic peptide
<220> FEATURE:
<221> NAME/KEY: PEPTIDE
<222> LOCATION: (373)..(404)
<223> OTHER INFORMATION: Mutant Tr6 T. rangeli trans-sialiadase -
      linker peptide
<220> FEATURE:
<221> NAME/KEY: PEPTIDE
<222> LOCATION: (405)..(638)
<223> OTHER INFORMATION: Mutant Tr6 T. rangeli trans-sialiadase -
      carbohydrate-binding peptide
```

<400> SEQUENCE: 2

```
Leu Ala Pro Gly Ser Ser Arg Val Glu Leu Phe Lys Arg Lys Asn Ser
 1               5                  10                  15

Thr Val Pro Phe Glu Glu Ser Asn Gly Thr Ile Arg Glu Arg Val Val
            20                  25                  30

His Ser Phe Arg Leu Pro Thr Ile Val Asn Val Asp Gly Val Met Val
        35                  40                  45

Ala Ile Ala Asp Ala Arg Tyr Glu Thr Ser Phe Asp Asn Ser Phe Ile
    50                  55                  60

Glu Thr Ala Val Lys Tyr Ser Val Asp Asp Gly Ala Thr Trp Asn Thr
65                  70                  75                  80

Gln Ile Ala Ile Lys Asn Ser Arg Ala Ser Ser Val Ser Arg Val Val
                85                  90                  95

Asp Pro Thr Val Ile Val Lys Gly Asn Lys Leu Tyr Ile Leu Val Gly
            100                 105                 110

Ser Phe Asn Lys Thr Arg Asn Tyr Trp Thr Gln His Arg Asp Gly Ser
        115                 120                 125

Asp Trp Glu Pro Leu Leu Val Val Gly Glu Val Thr Lys Ser Ala Ala
    130                 135                 140

Asn Gly Lys Thr Thr Ala Thr Ile Ser Trp Gly Lys Pro Val Ser Leu
145                 150                 155                 160

Lys Pro Leu Phe Pro Ala Glu Phe Asp Gly Ile Leu Thr Lys Glu Phe
                165                 170                 175

Val Gly Gly Val Gly Ala Ala Ile Val Ala Ser Asn Gly Asn Leu Val
            180                 185                 190

Tyr Pro Val Gln Ile Ala Asp Met Gly Gly Arg Val Phe Thr Lys Ile
        195                 200                 205

Met Tyr Ser Glu Asp Asp Gly Asn Thr Trp Lys Phe Ala Glu Gly Arg
    210                 215                 220

Ser Lys Phe Gly Cys Ser Glu Pro Ala Val Leu Glu Trp Glu Gly Lys
225                 230                 235                 240

Leu Ile Ile Asn Asn Arg Val Asp Tyr Asn Arg Arg Leu Val Tyr Glu
```

```
            245                 250                 255
Ser Ser Asp Met Gly Lys Thr Trp Val Glu Ala Leu Gly Thr Leu Ser
            260                 265                 270

His Val Trp Thr Asn Ser Pro Thr Ser Asn Gln Pro Asp Cys Gln Ser
            275                 280                 285

Ser Phe Val Ala Val Thr Ile Glu Gly Lys Arg Val Met Leu Phe Thr
            290                 295                 300

His Pro Leu Asn Leu Lys Gly Arg Trp Met Arg Asp Arg Leu His Leu
305                 310                 315                 320

Trp Met Thr Asp Asn Gln Arg Ile Phe Asp Val Gly Gln Ile Ser Ile
                325                 330                 335

Gly Asp Glu Asn Ser Gly Tyr Ser Ser Val Leu Tyr Lys Asp Asp Lys
                340                 345                 350

Leu Tyr Ser Leu His Glu Ile Asn Thr Asn Asp Val Tyr Ser Leu Val
            355                 360                 365

Phe Val Arg Leu Ile Gly Glu Leu Gln Leu Met Lys Ser Val Val Arg
        370                 375                 380

Thr Trp Lys Glu Glu Asp Asn His Leu Ala Ser Ile Cys Thr Pro Val
385                 390                 395                 400

Val Pro Ala Thr Pro Pro Ser Lys Gly Ala Cys Gly Ala Ala Val Pro
                405                 410                 415

Thr Ala Gly Leu Val Gly Phe Leu Ser His Ser Ala Asn Gly Ser Val
                420                 425                 430

Trp Glu Asp Val Tyr Arg Cys Val Asp Ala Asn Val Ala Asn Ala Glu
            435                 440                 445

Arg Val Pro Asn Gly Leu Lys Phe Asn Gly Val Gly Gly Ala Val
        450                 455                 460

Trp Pro Val Ala Arg Gln Gly Gln Thr Arg Arg Tyr Gln Phe Ala Asn
465                 470                 475                 480

Tyr Arg Phe Thr Leu Val Ala Thr Val Thr Ile Asp Glu Leu Pro Lys
                485                 490                 495

Gly Thr Ser Pro Leu Leu Gly Ala Gly Leu Glu Gly Pro Gly Asp Ala
                500                 505                 510

Lys Leu Leu Gly Leu Ser Tyr Asp Lys Asn Arg Gln Trp Arg Pro Leu
            515                 520                 525

Tyr Gly Ala Ala Pro Ala Ser Pro Thr Gly Ser Trp Glu Leu His Lys
        530                 535                 540

Lys Tyr His Val Val Leu Thr Met Ala Asp Arg Gln Gly Ser Val Tyr
545                 550                 555                 560

Val Asp Gly Gln Pro Leu Ala Gly Ser Gly Asn Thr Val Val Arg Gly
                565                 570                 575

Ala Thr Leu Pro Asp Ile Ser His Phe Tyr Ile Gly Pro Arg Ser
            580                 585                 590

Lys Gly Ala Pro Thr Asp Ser Arg Val Thr Val Thr Asn Val Val Leu
            595                 600                 605

Tyr Asn Arg Arg Leu Asn Ser Ser Glu Ile Arg Thr Leu Phe Leu Ser
        610                 615                 620

Gln Asp Met Ile Gly Thr Asp Gly Gly Ala Thr Ala Ala
625                 630                 635

<210> SEQ ID NO 3
<211> LENGTH: 1914
<212> TYPE: DNA
<213> ORGANISM: Trypanosoma rangeli
```

<220> FEATURE:
<221> NAME/KEY: CDS
<222> LOCATION: (1)..(1914)
<223> OTHER INFORMATION: CDS for Tr13 mutant R. rangeli trans-sialidase
      comprising: N-terminal region to catalytic domain peptide: aa
      residues 1-81; Catalytic domain peptide: aa residues 81-1116;
      Linker peptide: aa residues 1117-1212; CBD: aa residues 1213-1914.

<400> SEQUENCE: 3

| | | | | | | | | | | | | | | | | |
|---|---|---|---|---|---|---|---|---|---|---|---|---|---|---|---|---|
| ttg | gct | ccc | gga | tca | tct | cgt | gtg | gaa | tta | ttt | aaa | aga | aaa | aac | tcc | 48 |
| Leu | Ala | Pro | Gly | Ser | Ser | Arg | Val | Glu | Leu | Phe | Lys | Arg | Lys | Asn | Ser | |
| 1 | | | | 5 | | | | | 10 | | | | | 15 | | |
| acc | gtg | cca | ttt | gag | gag | tca | aac | ggt | act | ata | cga | gaa | cgt | gtg | gtt | 96 |
| Thr | Val | Pro | Phe | Glu | Glu | Ser | Asn | Gly | Thr | Ile | Arg | Glu | Arg | Val | Val | |
| | | | 20 | | | | | 25 | | | | | 30 | | | |
| cat | tca | ttt | aga | tta | cca | act | atc | gtt | aac | gta | gat | gga | gtc | atg | gtt | 144 |
| His | Ser | Phe | Arg | Leu | Pro | Thr | Ile | Val | Asn | Val | Asp | Gly | Val | Met | Val | |
| | | 35 | | | | | 40 | | | | | 45 | | | | |
| gcc | att | gct | gat | gcc | aga | tat | gag | aca | tca | ttc | gac | aac | tcc | ttt | atc | 192 |
| Ala | Ile | Ala | Asp | Ala | Arg | Tyr | Glu | Thr | Ser | Phe | Asp | Asn | Ser | Phe | Ile | |
| | 50 | | | | | 55 | | | | | 60 | | | | | |
| gaa | act | gct | gtt | aaa | tac | agt | gtt | gac | gat | ggt | gct | acg | tgg | aat | aca | 240 |
| Glu | Thr | Ala | Val | Lys | Tyr | Ser | Val | Asp | Asp | Gly | Ala | Thr | Trp | Asn | Thr | |
| 65 | | | | | 70 | | | | | 75 | | | | | 80 | |
| caa | att | gca | atc | aaa | aat | tct | cgt | gca | tca | tca | gtt | tca | agg | gtt | gtc | 288 |
| Gln | Ile | Ala | Ile | Lys | Asn | Ser | Arg | Ala | Ser | Ser | Val | Ser | Arg | Val | Val | |
| | | | | 85 | | | | | 90 | | | | | 95 | | |
| gat | cct | acg | gtc | ata | gta | aag | gga | aat | aag | ttg | tat | atc | ctg | gtt | gga | 336 |
| Asp | Pro | Thr | Val | Ile | Val | Lys | Gly | Asn | Lys | Leu | Tyr | Ile | Leu | Val | Gly | |
| | | | 100 | | | | | 105 | | | | | 110 | | | |
| tcc | ttt | aac | aag | aca | agg | aac | tat | tgg | acc | cag | cac | aga | gat | gga | tct | 384 |
| Ser | Phe | Asn | Lys | Thr | Arg | Asn | Tyr | Trp | Thr | Gln | His | Arg | Asp | Gly | Ser | |
| | | 115 | | | | | 120 | | | | | 125 | | | | |
| gac | tgg | gaa | cca | ttg | ttg | gtg | gtt | gga | gag | gtt | acg | aag | tct | gct | gct | 432 |
| Asp | Trp | Glu | Pro | Leu | Leu | Val | Val | Gly | Glu | Val | Thr | Lys | Ser | Ala | Ala | |
| | 130 | | | | | 135 | | | | | 140 | | | | | |
| aac | ggt | aaa | aca | act | gca | act | att | tca | tgg | ggg | aaa | cct | gtc | tcc | ctt | 480 |
| Asn | Gly | Lys | Thr | Thr | Ala | Thr | Ile | Ser | Trp | Gly | Lys | Pro | Val | Ser | Leu | |
| 145 | | | | | 150 | | | | | 155 | | | | | 160 | |
| aag | cct | ttg | ttc | cct | gca | gag | ttc | gac | ggc | ata | ctt | act | aag | gaa | ttc | 528 |
| Lys | Pro | Leu | Phe | Pro | Ala | Glu | Phe | Asp | Gly | Ile | Leu | Thr | Lys | Glu | Phe | |
| | | | | 165 | | | | | 170 | | | | | 175 | | |
| gta | ggt | gga | gta | ggc | gcc | gcc | atc | gtg | gca | agt | aat | ggt | aat | ttg | gta | 576 |
| Val | Gly | Gly | Val | Gly | Ala | Ala | Ile | Val | Ala | Ser | Asn | Gly | Asn | Leu | Val | |
| | | | 180 | | | | | 185 | | | | | 190 | | | |
| tac | cct | gtg | caa | gta | act | aat | aag | aag | aag | caa | gta | ttt | aca | aaa | att | 624 |
| Tyr | Pro | Val | Gln | Val | Thr | Asn | Lys | Lys | Lys | Gln | Val | Phe | Thr | Lys | Ile | |
| | | 195 | | | | | 200 | | | | | 205 | | | | |
| atg | tat | tcc | gag | gat | gat | ggt | aac | act | tgg | aag | ttc | gcc | gaa | gga | agg | 672 |
| Met | Tyr | Ser | Glu | Asp | Asp | Gly | Asn | Thr | Trp | Lys | Phe | Ala | Glu | Gly | Arg | |
| | 210 | | | | | 215 | | | | | 220 | | | | | |
| tct | aag | ttc | ggt | tgc | tca | gaa | cca | gca | gtt | ttg | gaa | tgg | gaa | gga | aag | 720 |
| Ser | Lys | Phe | Gly | Cys | Ser | Glu | Pro | Ala | Val | Leu | Glu | Trp | Glu | Gly | Lys | |
| 225 | | | | | 230 | | | | | 235 | | | | | 240 | |
| cta | atc | att | aat | aac | cga | gtc | gat | tac | aat | aga | cgt | ctg | gtg | tac | gaa | 768 |
| Leu | Ile | Ile | Asn | Asn | Arg | Val | Asp | Tyr | Asn | Arg | Arg | Leu | Val | Tyr | Glu | |
| | | | | 245 | | | | | 250 | | | | | 255 | | |
| tcc | agt | gac | atg | ggc | aaa | aca | tgg | gta | gag | gct | ctt | ggt | act | ctg | tcc | 816 |
| Ser | Ser | Asp | Met | Gly | Lys | Thr | Trp | Val | Glu | Ala | Leu | Gly | Thr | Leu | Ser | |
| | | | 260 | | | | | 265 | | | | | 270 | | | |
| cac | gtc | tgg | acg | aac | agt | cca | act | tcc | aat | caa | ccc | gat | tgt | cag | agt | 864 |

```
                His Val Trp Thr Asn Ser Pro Thr Ser Asn Gln Pro Asp Cys Gln Ser
                        275                 280                 285 tca ttc gtt gca gtt act atc gaa ggt aaa cga gtg atg ttg ttt act              912
Ser Phe Val Ala Val Thr Ile Glu Gly Lys Arg Val Met Leu Phe Thr
        290                 295                 300 cat cca cta aat ttg aag ggt aga tgg atg agg gat aga ctt cat ctg              960
His Pro Leu Asn Leu Lys Gly Arg Trp Met Arg Asp Arg Leu His Leu
305                 310                 315                 320 tgg atg acc gat aat cag aga atc ttt gat gtt ggc caa att tcc att             1008
Trp Met Thr Asp Asn Gln Arg Ile Phe Asp Val Gly Gln Ile Ser Ile
                325                 330                 335 ggt gat gaa aac agt ggt tac tct tcc gtc cta tac aag gac gat aaa             1056
Gly Asp Glu Asn Ser Gly Tyr Ser Ser Val Leu Tyr Lys Asp Asp Lys
        340                 345                 350 tta tat tcc cta cat gag att aat act aat gat gtt tat tct ctt gtt             1104
Leu Tyr Ser Leu His Glu Ile Asn Thr Asn Asp Val Tyr Ser Leu Val
355                 360                 365 ttt gtc cga ttg att ggt gag ctg cag tta atg aaa agt gtg gtt cgt             1152
Phe Val Arg Leu Ile Gly Glu Leu Gln Leu Met Lys Ser Val Val Arg
370                 375                 380 acc tgg aag gaa gag gac aat cat ttg gct tca ata tgt act cca gtc             1200
Thr Trp Lys Glu Glu Asp Asn His Leu Ala Ser Ile Cys Thr Pro Val
385                 390                 395                 400 gta cca gca acc cca cca agt aaa gga gcc tgc ggt gcc gct gta cct             1248
Val Pro Ala Thr Pro Pro Ser Lys Gly Ala Cys Gly Ala Ala Val Pro
                405                 410                 415 aca gct ggt tta gtt ggc ttc tta tct cac tca gct aat gga tcc gtt             1296
Thr Ala Gly Leu Val Gly Phe Leu Ser His Ser Ala Asn Gly Ser Val
        420                 425                 430 tgg gag gac gta tat aga tgt gtc gat gct aac gtc gcc aac gct gag             1344
Trp Glu Asp Val Tyr Arg Cys Val Asp Ala Asn Val Ala Asn Ala Glu
435                 440                 445 aga gtt cct aac ggc ctt aag ttt aat ggg gtt ggt ggg ggc gct gtc             1392
Arg Val Pro Asn Gly Leu Lys Phe Asn Gly Val Gly Gly Gly Ala Val
        450                 455                 460 tgg cca gtc gcc agg cag gga caa acc cga agg tac caa ttc gca aac             1440
Trp Pro Val Ala Arg Gln Gly Gln Thr Arg Arg Tyr Gln Phe Ala Asn
465                 470                 475                 480 tac aga ttt acc tta gtc gcc acc gtt acg att gac gaa ttg ccc aaa             1488
Tyr Arg Phe Thr Leu Val Ala Thr Val Thr Ile Asp Glu Leu Pro Lys
                485                 490                 495 ggt acc tct ccc ctt ctt ggt gcc ggg tta gaa ggt cca ggc gac gct             1536
Gly Thr Ser Pro Leu Leu Gly Ala Gly Leu Glu Gly Pro Gly Asp Ala
        500                 505                 510 aaa ttg cta ggt tta tct tac gac aag aac cgt caa tgg cga ccc ttg             1584
Lys Leu Leu Gly Leu Ser Tyr Asp Lys Asn Arg Gln Trp Arg Pro Leu
515                 520                 525 tac gga gca gcc cct gct tct cct aca gga tct tgg gag cta cac aag             1632
Tyr Gly Ala Ala Pro Ala Ser Pro Thr Gly Ser Trp Glu Leu His Lys
        530                 535                 540 aag tac cat gta gtc ctg acc atg gct gac aga cag ggg agt gtt tat             1680
Lys Tyr His Val Val Leu Thr Met Ala Asp Arg Gln Gly Ser Val Tyr
545                 550                 555                 560 gtt gat ggg caa cct ctt gcc gga tca ggc aat acc gtg gtt aga gga             1728
Val Asp Gly Gln Pro Leu Ala Gly Ser Gly Asn Thr Val Val Arg Gly
                565                 570                 575 gct act ttg cca gac atc tct cac ttc tac att ggt gga ccc aga tct            1776
Ala Thr Leu Pro Asp Ile Ser His Phe Tyr Ile Gly Gly Pro Arg Ser
        580                 585                 590
```

| | | | | | | | | | | | | | | | |
|---|---|---|---|---|---|---|---|---|---|---|---|---|---|---|---|
| aag | gga | gcc | cct | aca | gat | agt | aga | gtt | aca | gtg | act | aac | gtg | gtt | tta | 1824 |
| Lys | Gly | Ala | Pro | Thr | Asp | Ser | Arg | Val | Thr | Val | Thr | Asn | Val | Val | Leu | |
| | 595 | | | | | 600 | | | | | 605 | | | | | |

| tat | aat | cgt | aga | ctg | aac | tct | agt | gag | atc | cgt | aca | ctt | ttt | ttg | tct | 1872 |
|---|---|---|---|---|---|---|---|---|---|---|---|---|---|---|---|---|
| Tyr | Asn | Arg | Arg | Leu | Asn | Ser | Ser | Glu | Ile | Arg | Thr | Leu | Phe | Leu | Ser | |
| 610 | | | | | 615 | | | | | 620 | | | | | | |

| caa | gac | atg | ata | ggt | acc | gat | ggt | gga | gct | ggt | aca | gca | gca | | | 1914 |
|---|---|---|---|---|---|---|---|---|---|---|---|---|---|---|---|---|
| Gln | Asp | Met | Ile | Gly | Thr | Asp | Gly | Gly | Ala | Gly | Thr | Ala | Ala | | | |
| 625 | | | | 630 | | | | | 635 | | | | | | | |

<210> SEQ ID NO 4
<211> LENGTH: 638
<212> TYPE: PRT
<213> ORGANISM: Trypanosoma rangeli

<400> SEQUENCE: 4

Leu Ala Pro Gly Ser Ser Arg Val Glu Leu Phe Lys Arg Lys Asn Ser
1               5                   10                  15

Thr Val Pro Phe Glu Glu Ser Asn Gly Thr Ile Arg Glu Arg Val Val
            20                  25                  30

His Ser Phe Arg Leu Pro Thr Ile Val Asn Val Asp Gly Val Met Val
        35                  40                  45

Ala Ile Ala Asp Ala Arg Tyr Glu Thr Ser Phe Asp Asn Ser Phe Ile
    50                  55                  60

Glu Thr Ala Val Lys Tyr Ser Val Asp Asp Gly Ala Thr Trp Asn Thr
65                  70                  75                  80

Gln Ile Ala Ile Lys Asn Ser Arg Ala Ser Ser Val Ser Arg Val Val
                85                  90                  95

Asp Pro Thr Val Ile Val Lys Gly Asn Lys Leu Tyr Ile Leu Val Gly
            100                 105                 110

Ser Phe Asn Lys Thr Arg Asn Tyr Trp Thr Gln His Arg Asp Gly Ser
        115                 120                 125

Asp Trp Glu Pro Leu Leu Val Val Gly Glu Val Thr Lys Ser Ala Ala
    130                 135                 140

Asn Gly Lys Thr Thr Ala Thr Ile Ser Trp Gly Lys Pro Val Ser Leu
145                 150                 155                 160

Lys Pro Leu Phe Pro Ala Glu Phe Asp Gly Ile Leu Thr Lys Glu Phe
                165                 170                 175

Val Gly Gly Val Gly Ala Ala Ile Val Ala Ser Asn Gly Asn Leu Val
            180                 185                 190

Tyr Pro Val Gln Val Thr Asn Lys Lys Gln Val Phe Thr Lys Ile
        195                 200                 205

Met Tyr Ser Glu Asp Asp Gly Asn Thr Trp Lys Phe Ala Glu Gly Arg
    210                 215                 220

Ser Lys Phe Gly Cys Ser Glu Pro Ala Val Leu Glu Trp Glu Gly Lys
225                 230                 235                 240

Leu Ile Ile Asn Asn Arg Val Asp Tyr Asn Arg Arg Leu Val Tyr Glu
                245                 250                 255

Ser Ser Asp Met Gly Lys Thr Trp Val Glu Ala Leu Gly Thr Leu Ser
            260                 265                 270

His Val Trp Thr Asn Ser Pro Thr Ser Asn Gln Pro Asp Cys Gln Ser
        275                 280                 285

Ser Phe Val Ala Val Thr Ile Glu Gly Lys Arg Val Met Leu Phe Thr
    290                 295                 300

His Pro Leu Asn Leu Lys Gly Arg Trp Met Arg Asp Arg Leu His Leu
305                 310                 315                 320

```
Trp Met Thr Asp Asn Gln Arg Ile Phe Asp Val Gly Gln Ile Ser Ile
                325                 330                 335

Gly Asp Glu Asn Ser Gly Tyr Ser Ser Val Leu Tyr Lys Asp Asp Lys
            340                 345                 350

Leu Tyr Ser Leu His Glu Ile Asn Thr Asn Asp Val Tyr Ser Leu Val
        355                 360                 365

Phe Val Arg Leu Ile Gly Glu Leu Gln Leu Met Lys Ser Val Val Arg
    370                 375                 380

Thr Trp Lys Glu Glu Asp Asn His Leu Ala Ser Ile Cys Thr Pro Val
385                 390                 395                 400

Val Pro Ala Thr Pro Pro Ser Lys Gly Ala Cys Gly Ala Ala Val Pro
                405                 410                 415

Thr Ala Gly Leu Val Gly Phe Leu Ser His Ser Ala Asn Gly Ser Val
            420                 425                 430

Trp Glu Asp Val Tyr Arg Cys Val Asp Ala Asn Val Ala Asn Ala Glu
        435                 440                 445

Arg Val Pro Asn Gly Leu Lys Phe Asn Gly Val Gly Gly Gly Ala Val
    450                 455                 460

Trp Pro Val Ala Arg Gln Gly Gln Thr Arg Arg Tyr Gln Phe Ala Asn
465                 470                 475                 480

Tyr Arg Phe Thr Leu Val Ala Thr Val Thr Ile Asp Glu Leu Pro Lys
                485                 490                 495

Gly Thr Ser Pro Leu Leu Gly Ala Gly Leu Glu Gly Pro Gly Asp Ala
            500                 505                 510

Lys Leu Leu Gly Leu Ser Tyr Asp Lys Asn Arg Gln Trp Arg Pro Leu
        515                 520                 525

Tyr Gly Ala Ala Pro Ala Ser Pro Thr Gly Ser Trp Glu Leu His Lys
    530                 535                 540

Lys Tyr His Val Val Leu Thr Met Ala Asp Arg Gln Gly Ser Val Tyr
545                 550                 555                 560

Val Asp Gly Gln Pro Leu Ala Gly Ser Gly Asn Thr Val Val Arg Gly
                565                 570                 575

Ala Thr Leu Pro Asp Ile Ser His Phe Tyr Ile Gly Pro Arg Ser
            580                 585                 590

Lys Gly Ala Pro Thr Asp Ser Arg Val Thr Val Thr Asn Val Val Leu
        595                 600                 605

Tyr Asn Arg Arg Leu Asn Ser Ser Glu Ile Arg Thr Leu Phe Leu Ser
    610                 615                 620

Gln Asp Met Ile Gly Thr Asp Gly Gly Ala Gly Thr Ala Ala
625                 630                 635
```

<210> SEQ ID NO 5
<211> LENGTH: 345
<212> TYPE: PRT
<213> ORGANISM: Trypanosoma cruzi
<220> FEATURE:
<221> NAME/KEY: PEPTIDE
<222> LOCATION: (1)..(345)
<223> OTHER INFORMATION: Catalytic domain of T. cruzi trans-sialidase
      [Q26966]

<400> SEQUENCE: 5

```
Thr Glu Arg Val Val His Ser Phe Arg Leu Pro Ala Leu Val Asn Val
1               5                   10                  15

Asp Gly Val Met Val Ala Ile Ala Asp Ala Arg Tyr Glu Thr Ser Asn
            20                  25                  30
```

Asp Asn Ser Leu Ile Asp Thr Val Ala Lys Tyr Ser Val Asp Asp Gly
            35                  40                  45

Glu Thr Trp Glu Thr Gln Ile Ala Ile Lys Asn Ser Arg Ala Ser Ser
 50                  55                  60

Val Ser Arg Val Val Asp Pro Thr Val Ile Val Lys Gly Asn Lys Leu
 65                  70                  75                  80

Tyr Val Leu Val Gly Ser Tyr Asn Ser Ser Arg Ser Tyr Trp Thr Ser
                 85                  90                  95

His Gly Asp Ala Arg Asp Trp Asp Ile Leu Leu Ala Val Gly Glu Val
            100                 105                 110

Thr Lys Ser Thr Ala Gly Gly Lys Ile Thr Ala Ser Ile Lys Trp Gly
            115                 120                 125

Ser Pro Val Ser Leu Lys Glu Phe Phe Pro Ala Glu Met Glu Gly Met
130                 135                 140

His Thr Asn Gln Phe Leu Gly Ala Gly Val Ala Ile Val Ala Ser
145                 150                 155                 160

Asn Gly Asn Leu Val Tyr Pro Val Gln Val Thr Asn Lys Lys Lys Gln
                165                 170                 175

Val Phe Ser Lys Ile Phe Tyr Ser Glu Asp Glu Gly Lys Thr Trp Lys
            180                 185                 190

Phe Gly Lys Gly Arg Ser Ala Phe Gly Cys Ser Glu Pro Val Ala Leu
            195                 200                 205

Glu Trp Glu Gly Lys Leu Ile Ile Asn Thr Arg Val Asp Tyr Arg Arg
210                 215                 220

Arg Leu Val Tyr Glu Ser Ser Asp Met Gly Asn Ser Trp Leu Glu Ala
225                 230                 235                 240

Val Gly Thr Leu Ser Arg Val Trp Gly Pro Ser Pro Lys Ser Asn Gln
                245                 250                 255

Pro Gly Ser Gln Ser Ser Phe Thr Ala Val Thr Ile Glu Gly Met Arg
            260                 265                 270

Val Met Leu Phe Thr His Pro Leu Asn Phe Lys Gly Arg Trp Leu Arg
            275                 280                 285

Asp Arg Leu Asn Leu Trp Leu Thr Asp Asn Gln Arg Ile Tyr Asn Val
290                 295                 300

Gly Gln Val Ser Ile Gly Asp Glu Asn Ser Ala Tyr Ser Ser Val Leu
305                 310                 315                 320

Tyr Lys Asp Asp Lys Leu Tyr Cys Leu His Glu Ile Asn Ser Asn Glu
                325                 330                 335

Val Tyr Ser Leu Val Phe Ala Arg Leu
            340                 345

<210> SEQ ID NO 6
<211> LENGTH: 347
<212> TYPE: PRT
<213> ORGANISM: Trypanosoma congolense
<220> FEATURE:
<221> NAME/KEY: PEPTIDE
<222> LOCATION: (1)..(347)
<223> OTHER INFORMATION: Catalytic domain of T. congolese
      trans-sialidase [G0WJG3]

<400> SEQUENCE: 6

Gly Thr Thr Met Arg Thr Val His Ser Tyr Arg Ile Pro Ser Ile Val
1               5                   10                  15

Glu Val Gly Gly Val Leu Met Cys Val Gly Asp Ala Arg Tyr Ile Thr
            20                  25                  30

-continued

```
Ser Thr Asp Tyr Phe Phe Thr Asp Thr Val Ala Ala Tyr Ser Thr Asp
            35                  40                  45

Gly Gly Arg Thr Trp Lys Arg Glu Val Ile Ile Pro Asn Gly Arg Val
 50                  55                  60

Asp Ala His Tyr Ser Arg Val Val Asp Pro Thr Val Val Ala Lys Gly
 65                  70                  75                  80

Asn Asn Ile Tyr Val Leu Val Gly Arg Tyr Asn Val Thr Arg Gly Tyr
                    85                  90                  95

Trp His Asn Lys Asn Asn Arg Ala Gly Val Ala Asp Trp Glu Pro Phe
                100                 105                 110

Val Tyr Lys Gly Thr Val Asn Val Gly Thr Lys Asp Asn Ala Thr Asp
            115                 120                 125

Val Ser Ile Ser Trp Glu Arg Thr Ala Leu Lys Ser Leu Tyr Asn Phe
130                 135                 140

Pro Val Ser Gly Ser Pro Gly Thr Gln Phe Leu Gly Gly Ala Gly Gly
145                 150                 155                 160

Gly Val Val Thr Ser Asn Gly Thr Ile Val Leu Pro Val Gln Ala Arg
                165                 170                 175

Asn Lys Ala Asn Arg Val Val Ser Met Ile Leu Tyr Ser Ala Asp Asp
            180                 185                 190

Gly Lys Ser Trp His Phe Gly Lys Gly Glu Ala Gly Val Gly Thr Ser
            195                 200                 205

Glu Ala Ala Leu Thr Glu Trp Asp Gly Lys Leu Leu Ile Ser Ala Arg
210                 215                 220

Ser Asp Gly Gly Gln Gly Tyr Arg Met Ile Phe Glu Ser Ser Asp Leu
225                 230                 235                 240

Gly Ala Thr Trp Lys Glu Met Leu Asn Ser Ile Ser Arg Val Ile Gly
                245                 250                 255

Asn Ser Pro Gly Arg Ser Gly Pro Gly Ser Ser Ser Gly Phe Ile Thr
            260                 265                 270

Val Thr Val Glu Gly Val Pro Val Met Leu Leu Thr His Pro Lys Asn
            275                 280                 285

Leu Lys Gly Ser Tyr Tyr Arg Asp Arg Leu Gln Met Trp Met Thr Asp
290                 295                 300

Gly Asn Arg Met Trp His Val Gly Gln Val Ser Glu Gly Asp Asp Asn
305                 310                 315                 320

Ser Ala Tyr Ser Ser Leu Leu Tyr Thr Pro Asp Gly Val Leu Tyr Cys
                325                 330                 335

Leu His Glu Gln Asn Ile Asp Glu Val Tyr Ser
            340                 345
```

<210> SEQ ID NO 7
<211> LENGTH: 355
<212> TYPE: PRT
<213> ORGANISM: Trypanosoma brucei
<220> FEATURE:
<221> NAME/KEY: PEPTIDE
<222> LOCATION: (1)..(355)
<223> OTHER INFORMATION: Catalytic domain of T. brucei trans-sialidase
      [Q57XJ2]

<400> SEQUENCE: 7

```
Arg Thr Val His Ser Phe Arg Ile Pro Ser Phe Val Glu Val Asp Gly
 1               5                  10                  15

Val Leu Met Gly Ile Gly Asp Ala Arg Tyr Leu Thr Ser Thr Asp Tyr
            20                  25                  30
```

```
Phe Phe Thr Asp Thr Val Ala Lys Tyr Ser Ala Asp Gly Lys Thr
        35                  40                  45

Trp Lys Thr Glu Val Ile Ile Glu Asn Gly Arg Val Asp Pro Thr Tyr
         50                  55                  60

Ser Arg Val Val Asp Pro Thr Val Val Ala Lys Ala Asp Ser Val Phe
 65                  70                  75                  80

Val Leu Val Ala Arg Tyr Asn Val Thr Lys Gly Tyr Trp His Asn Glu
                 85                  90                  95

Asn Asn Ala Ala Gly Ile Ala Asp Trp Glu Pro Phe Met Tyr Lys Gly
                100                 105                 110

Val Val Thr Lys Gly Ala Asp Gly Lys Thr Ser Asp Val Arg Ile Ser
                115                 120                 125

Trp Thr Lys Thr Pro Leu Lys Pro Leu Tyr Asp Phe Thr Val Ala Gly
        130                 135                 140

Ser Lys Gly Thr Gln Phe Ile Gly Gly Ala Gly Asn Gly Val Val Thr
145                 150                 155                 160

Leu Asn Gly Thr Ile Leu Phe Pro Val Gln Ala Arg Asn Glu Asp Asn
                165                 170                 175

Ala Val Val Ser Met Val Met Tyr Ser Val Asp Asp Gly Val Ser Trp
                180                 185                 190

His Phe Ala Arg Gly Glu Thr Ala Leu Leu Thr Ser Glu Ala Ser Leu
                195                 200                 205

Thr Glu Trp Asn Gly Lys Leu Leu Met Ser Ala Arg Thr Asp Thr Ser
        210                 215                 220

Gly Val Asn Val Glu Gly Gly Phe Arg Lys Val Phe Glu Ser Asn Asn
225                 230                 235                 240

Leu Gly Ala Thr Trp Glu Glu Ser Leu Gly Thr Ile Ser Arg Val Ile
                245                 250                 255

Gly Asn Ser Pro Asp Arg Thr Lys Pro Ser Pro Thr Ala Asn Tyr Pro
                260                 265                 270

Gly Ser Ser Gly Ala Leu Ile Thr Val Thr Leu Gly Asp Val Pro Val
            275                 280                 285

Met Leu Ile Thr His Pro Lys Asn Thr Lys Gly Ala Trp Ser Arg Asp
        290                 295                 300

Arg Leu Gln Leu Trp Met Thr Asp Gly Asn Arg Met Trp Leu Val Gly
305                 310                 315                 320

Gln Ile Ser Glu Gly Asp Asp Asn Ser Ala Tyr Ser Ser Leu Leu Leu
                325                 330                 335

Ala Arg Asp Gly Leu Leu Tyr Cys Leu His Glu Gln Asn Ile Asp Glu
            340                 345                 350

Val Tyr Gly
        355

<210> SEQ ID NO 8
<211> LENGTH: 270
<212> TYPE: PRT
<213> ORGANISM: Trypanosoma cruzi
<220> FEATURE:
<221> NAME/KEY: PEPTIDE
<222> LOCATION: (1)..(270)
<223> OTHER INFORMATION: C-terminal region (linker and CBD peptide) of
      T. cruzi trans-sialidase [Q26966]

<400> SEQUENCE: 8

Val Gly Glu Leu Arg Ile Ile Lys Ser Val Leu Gln Ser Trp Lys Asn
1               5                  10                  15
```

```
Trp Asp Ser His Leu Ser Ser Ile Cys Thr Pro Ala Asp Pro Ala Ala
             20                  25                  30

Ser Ser Ser Glu Arg Gly Cys Gly Pro Ala Val Thr Thr Val Gly Leu
         35                  40                  45

Val Gly Phe Leu Ser His Ser Ala Thr Lys Thr Glu Trp Glu Asp Ala
 50                  55                  60

Tyr Arg Cys Val Asn Ala Ser Thr Ala Asn Ala Glu Arg Val Pro Asn
 65                  70                  75                  80

Gly Leu Lys Phe Ala Gly Val Gly Gly Ala Leu Trp Pro Val Ser
             85                  90                  95

Gln Gln Gly Gln Asn Gln Arg Tyr Arg Phe Ala Asn His Ala Phe Thr
         100                 105                 110

Val Val Ala Ser Val Thr Ile His Glu Val Pro Ser Val Ala Ser Pro
         115                 120                 125

Leu Leu Gly Ala Ser Leu Asp Ser Ser Gly Gly Lys Lys Leu Leu Gly
 130                 135                 140

Leu Ser Tyr Asp Glu Arg His Gln Trp Gln Pro Ile Tyr Gly Ser Thr
145                 150                 155                 160

Pro Val Thr Pro Thr Gly Ser Trp Glu Met Gly Lys Arg Tyr His Val
             165                 170                 175

Val Leu Thr Met Ala Asn Lys Ile Gly Ser Glu Tyr Ile Asp Gly Glu
         180                 185                 190

Pro Leu Glu Gly Ser Gly Gln Thr Val Val Pro Asp Glu Arg Thr Pro
         195                 200                 205

Asp Ile Ser His Phe Tyr Val Gly Gly Tyr Lys Arg Ser Asp Met Pro
 210                 215                 220

Thr Ile Ser His Val Thr Val Asn Asn Val Leu Leu Tyr Asn Arg Gln
225                 230                 235                 240

Leu Asn Ala Glu Glu Ile Arg Thr Leu Phe Leu Ser Gln Asp Leu Ile
             245                 250                 255

Gly Thr Glu Ala His Met Asp Ser Ser Ser Asp Thr Ser Ala
             260                 265                 270

<210> SEQ ID NO 9
<211> LENGTH: 250
<212> TYPE: PRT
<213> ORGANISM: Trypanosoma congolense
<220> FEATURE:
<221> NAME/KEY: PEPTIDE
<222> LOCATION: (1)..(250)
<223> OTHER INFORMATION: C-terminal region (linker and CBD peptide) of
      T. congolese trans-sialidase [G0WJG3]

<400> SEQUENCE: 9

Val Asp Glu Leu Lys Ser Ile Lys Ser Thr Ala Leu Val Trp Lys Ala
 1               5                  10                  15

Gln Asp Glu Leu Leu Leu Gly Asn Cys Leu Pro Gly Asp Lys Tyr Asp
             20                  25                  30

Pro Gly Cys Asp Gly Ile Pro Thr Ala Gly Leu Ala Gly Leu Leu Val
         35                  40                  45

Gly Pro Leu Thr Glu Lys Thr Trp Pro Asp Ala Tyr Arg Cys Val Asn
 50                  55                  60

Ala Ala Thr Ser Gly Ala Val Ser Thr Ala Glu Gly Val Arg Leu Asp
 65                  70                  75                  80

Val Gly Gly Gly Gly His Val Val Trp Pro Val Ser Glu Gln Gly Gln
             85                  90                  95
```

```
Asp Gln Arg Tyr Tyr Phe Thr Asn Ser Glu Phe Thr Leu Ala Val Thr
                100                 105                 110

Val Arg Phe Asp Glu Met Pro Gln Gly Glu Leu Pro Leu Leu Gly Phe
            115                 120                 125

Val Asn Arg Glu Gly Lys Val Lys Ile Leu Lys Val Ser Leu Ser
        130                 135                 140

Gly Val Glu Trp Leu Leu Ala Tyr Gly Asn Glu Tyr Asn Ser Thr Ala
145                 150                 155                 160

Ala Glu Pro Leu Asp Val Asn Glu Ser His Gln Val Leu Ala Leu
                165                 170                 175

His Asp Gly Ile Val Ser Leu His Val Asp Gly Gly Asn Thr Thr Ala
                180                 185                 190

Thr Val Ser Val Arg Val Ala Ser Pro Ala Glu Leu Leu Asn Ile His
            195                 200                 205

His Leu Phe Val Gly Thr Pro Val Asp Gly Gly Ala Lys Glu His Ala
        210                 215                 220

Asn Ile Thr Val Ser Asn Val Leu Val Tyr Asn Arg Pro Leu Arg Gly
225                 230                 235                 240

Val Glu Leu Leu Gly Leu Phe Ala Asn Arg
                245                 250
```

<210> SEQ ID NO 10
<211> LENGTH: 284
<212> TYPE: PRT
<213> ORGANISM: Trypanosoma brucei
<220> FEATURE:
<221> NAME/KEY: PEPTIDE
<222> LOCATION: (1)..(284)
<223> OTHER INFORMATION: C-terminal region (linker and CBD peptide) of
      T. brucei trans-sialidase [Q57XJ2]

<400> SEQUENCE: 10

```
Val Asp Glu Leu Glu Lys Val Asn Ala Thr Val Arg Lys Trp Lys Ala
1               5                   10                  15

Gln Asp Ala Leu Leu Ala Gly Leu Cys Ser Ser Ser Arg Lys Lys Asn
                20                  25                  30

Asp Pro Thr Cys Ser Gly Val Pro Thr Asp Gly Leu Val Gly Leu Leu
            35                  40                  45

Ala Gly Pro Val Gly Ala Ser Val Trp Ala Asp Val Tyr Asp Cys Val
50                  55                  60

Asn Ala Ser Ile Ser Asp Gly Val Lys Val Ser Glu Gly Val Gln Leu
65                  70                  75                  80

Gly Gly Lys Arg Asn Ser Arg Val Leu Trp Pro Val Ser Glu Gln Gly
                85                  90                  95

Gln Asp Gln Arg Tyr Tyr Phe Ala Asn Thr His Phe Thr Leu Leu Ala
                100                 105                 110

Thr Val Arg Phe Ala Gly Glu Pro Lys Ala Glu Ala Pro Leu Met Gly
            115                 120                 125

Phe Ser Asn Ala Glu Gly Lys Thr Ser Glu Thr Leu Ser Leu Thr Val
        130                 135                 140

Gly Gly Lys Lys Trp Val Leu Thr Tyr Gly Ser Val Arg Lys Glu Gly
145                 150                 155                 160

Pro Thr Thr Ser Met Asp Trp Asn Gln Thr His Gln Ile Ala Leu Thr
                165                 170                 175

Leu Arg Asp Gly Lys Val Asp Ala His Val Asn Gly Glu Leu Ile Ile
            180                 185                 190
```

```
Lys Glu Val Ser Val Gly Ala Ser Glu Ser Ser Ala His Leu His Leu
            195                 200                 205

Ser His Phe Phe Ile Gly Ala Pro Val Asn Asp Ser Gly Glu Gly Gly
            210                 215                 220

Asn Asn Val Ile Val Arg Asn Val Leu Leu Tyr Asn Arg Lys Leu Asp
225                 230                 235                 240

Glu Asp Glu Leu Gln Leu Leu Tyr Ser Asn Arg Glu Lys Ile Gln Pro
                245                 250                 255

Val Val Ser Ala Val Gly Ile Pro Glu Gly Met Ser Ala Pro Arg Leu
            260                 265                 270

Cys Cys Leu Leu Ile Leu Met Tyr Val Leu Ala Ile
            275                 280

<210> SEQ ID NO 11
<211> LENGTH: 2259
<212> TYPE: DNA
<213> ORGANISM: Trypanosoma rangeli
<220> FEATURE:
<221> NAME/KEY: CDS
<222> LOCATION: (1)..(273)
<223> OTHER INFORMATION: Nt 1-273 encode a-factor signal sequence; Kex2
      and Ste3 sites;
<220> FEATURE:
<221> NAME/KEY: CDS
<222> LOCATION: (274)..(2187)
<223> OTHER INFORMATION: Nt 274-2187 encode Tr13 mutant trans-sialidase;
<220> FEATURE:
<221> NAME/KEY: CDS
<222> LOCATION: (2188)..(2259)
<223> OTHER INFORMATION: Nt 274-2187 encode a C-terminal c-myc-tag and
      His-tag.;

<400> SEQUENCE: 11 atg aga ttt cct tca att ttt act gct gtt tta ttc gca gca tcc tcc      48
Met Arg Phe Pro Ser Ile Phe Thr Ala Val Leu Phe Ala Ala Ser Ser
1               5                   10                  15 gca tta gct gct cca gtc aac act aca aca gaa gat gaa acg gca caa      96
Ala Leu Ala Ala Pro Val Asn Thr Thr Thr Glu Asp Glu Thr Ala Gln
                20                  25                  30 att ccg gct gaa gct gtc atc ggt tac tca gat tta gaa ggg gat ttc     144
Ile Pro Ala Glu Ala Val Ile Gly Tyr Ser Asp Leu Glu Gly Asp Phe
            35                  40                  45 gat gtt gct gtt ttg cca ttt tcc aac agc aca aat aac ggg tta ttg     192
Asp Val Ala Val Leu Pro Phe Ser Asn Ser Thr Asn Asn Gly Leu Leu
        50                  55                  60 ttt ata aat act act att gcc agc att gct gct aaa gaa gaa ggg gta     240
Phe Ile Asn Thr Thr Ile Ala Ser Ile Ala Ala Lys Glu Glu Gly Val
65                  70                  75                  80 tct ctc gag aag aga gag gct gaa gct gct tct ttg gct ccc gga tca     288
Ser Leu Glu Lys Arg Glu Ala Glu Ala Ala Ser Leu Ala Pro Gly Ser
                85                  90                  95 tct cgt gtg gaa tta ttt aaa aga aaa aac tcc acc gtg cca ttt gag     336
Ser Arg Val Glu Leu Phe Lys Arg Lys Asn Ser Thr Val Pro Phe Glu
                100                 105                 110 gag tca aac ggt act ata cga gaa cgt gtg gtt cat tca ttt aga tta     384
Glu Ser Asn Gly Thr Ile Arg Glu Arg Val Val His Ser Phe Arg Leu
            115                 120                 125 cca act atc gtt aac gta gat gga gtc atg gtt gcc att gct gat gcc     432
Pro Thr Ile Val Asn Val Asp Gly Val Met Val Ala Ile Ala Asp Ala
        130                 135                 140 aga tat gag aca tca ttc gac aac tcc ttt atc gaa act gct gtt aaa     480
Arg Tyr Glu Thr Ser Phe Asp Asn Ser Phe Ile Glu Thr Ala Val Lys
145                 150                 155                 160
```

```
                145                 150                 155                 160
tac agt gtt gac gat ggt gct acg tgg aat aca caa att gca atc aaa    528
Tyr Ser Val Asp Asp Gly Ala Thr Trp Asn Thr Gln Ile Ala Ile Lys
                165                 170                 175 aat tct cgt gca tca tca gtt tca agg gtt gtc gat cct acg gtc ata    576
Asn Ser Arg Ala Ser Ser Val Ser Arg Val Val Asp Pro Thr Val Ile
            180                 185                 190 gta aag gga aat aag ttg tat atc ctg gtt gga tcc ttt aac aag aca    624
Val Lys Gly Asn Lys Leu Tyr Ile Leu Val Gly Ser Phe Asn Lys Thr
        195                 200                 205 agg aac tat tgg acc cag cac aga gat gga tct gac tgg gaa cca ttg    672
Arg Asn Tyr Trp Thr Gln His Arg Asp Gly Ser Asp Trp Glu Pro Leu
    210                 215                 220 ttg gtg gtt gga gag gtt acg aag tct gct gct aac ggt aaa aca act    720
Leu Val Val Gly Glu Val Thr Lys Ser Ala Ala Asn Gly Lys Thr Thr
225                 230                 235                 240 gca act att tca tgg ggg aaa cct gtc tcc ctt aag cct ttg ttc cct    768
Ala Thr Ile Ser Trp Gly Lys Pro Val Ser Leu Lys Pro Leu Phe Pro
                245                 250                 255 gca gag ttc gac ggc ata ctt act aag gaa ttc gta ggt gga gta ggc    816
Ala Glu Phe Asp Gly Ile Leu Thr Lys Glu Phe Val Gly Gly Val Gly
            260                 265                 270 gcc gcc atc gtg gca agt aat ggt aat ttg gta tac cct gtg caa gta    864
Ala Ala Ile Val Ala Ser Asn Gly Asn Leu Val Tyr Pro Val Gln Val
        275                 280                 285 act aat aag aag aag caa gta ttt aca aaa att atg tat tcc gag gat    912
Thr Asn Lys Lys Lys Gln Val Phe Thr Lys Ile Met Tyr Ser Glu Asp
    290                 295                 300 gat ggt aac act tgg aag ttc gcc gaa gga agg tct aag ttc ggt tgc    960
Asp Gly Asn Thr Trp Lys Phe Ala Glu Gly Arg Ser Lys Phe Gly Cys
305                 310                 315                 320 tca gaa cca gca gtt ttg gaa tgg gaa gga aag cta atc att aat aac    1008
Ser Glu Pro Ala Val Leu Glu Trp Glu Gly Lys Leu Ile Ile Asn Asn
                325                 330                 335 cga gtc gat tac aat aga cgt ctg gtg tac gaa tcc agt gac atg ggc    1056
Arg Val Asp Tyr Asn Arg Arg Leu Val Tyr Glu Ser Ser Asp Met Gly
            340                 345                 350 aaa aca tgg gta gag gct ctt ggt act ctg tcc cac gtc tgg acg aac    1104
Lys Thr Trp Val Glu Ala Leu Gly Thr Leu Ser His Val Trp Thr Asn
        355                 360                 365 agt cca act tcc aat caa ccc gat tgt cag agt tca ttc gtt gca gtt    1152
Ser Pro Thr Ser Asn Gln Pro Asp Cys Gln Ser Ser Phe Val Ala Val
    370                 375                 380 act atc gaa ggt aaa cga gtg atg ttg ttt act cat cca cta aat ttg    1200
Thr Ile Glu Gly Lys Arg Val Met Leu Phe Thr His Pro Leu Asn Leu
385                 390                 395                 400 aag ggt aga tgg atg agg gat aga ctt cat ctg tgg atg acc gat aat    1248
Lys Gly Arg Trp Met Arg Asp Arg Leu His Leu Trp Met Thr Asp Asn
                405                 410                 415 cag aga atc ttt gat gtt ggc caa att tcc att ggt gat gaa aac agt    1296
Gln Arg Ile Phe Asp Val Gly Gln Ile Ser Ile Gly Asp Glu Asn Ser
            420                 425                 430 ggt tac tct tcc gtc cta tac aag gac gat aaa tta tat tcc cta cat    1344
Gly Tyr Ser Ser Val Leu Tyr Lys Asp Asp Lys Leu Tyr Ser Leu His
        435                 440                 445 gag att aat act aat gat gtt tat tct ctt gtt ttt gtc cga ttg att    1392
Glu Ile Asn Thr Asn Asp Val Tyr Ser Leu Val Phe Val Arg Leu Ile
    450                 455                 460 ggt gag ctg cag tta atg aaa agt gtg gtt cgt acc tgg aag gaa gag    1440
Gly Glu Leu Gln Leu Met Lys Ser Val Val Arg Thr Trp Lys Glu Glu
```

| | | | | | | | | | | | | | | |
|---|---|---|---|---|---|---|---|---|---|---|---|---|---|---|
| Gly | Glu | Leu | Gln | Leu | Met | Lys | Ser | Val | Val | Arg | Thr | Trp | Lys | Glu |
| 465 | | | | | 470 | | | | 475 | | | | | 480 |

```
gac aat cat ttg gct tca ata tgt act cca gtc gta cca gca acc cca    1488
Asp Asn His Leu Ala Ser Ile Cys Thr Pro Val Val Pro Ala Thr Pro
            485                 490                 495 cca agt aaa gga gcc tgc ggt gcc gct gta cct aca gct ggt tta gtt    1536
Pro Ser Lys Gly Ala Cys Gly Ala Ala Val Pro Thr Ala Gly Leu Val
        500                 505                 510 ggc ttc tta tct cac tca gct aat gga tcc gtt tgg gag gac gta tat    1584
Gly Phe Leu Ser His Ser Ala Asn Gly Ser Val Trp Glu Asp Val Tyr
            515                 520                 525 aga tgt gtc gat gct aac gtc gcc aac gct gag aga gtt cct aac ggc    1632
Arg Cys Val Asp Ala Asn Val Ala Asn Ala Glu Arg Val Pro Asn Gly
        530                 535                 540 ctt aag ttt aat ggg gtt ggt ggg ggc gct gtc tgg cca gtc gcc agg    1680
Leu Lys Phe Asn Gly Val Gly Gly Gly Ala Val Trp Pro Val Ala Arg
545                 550                 555                 560 cag gga caa acc cga agg tac caa ttc gca aac tac aga ttt acc tta    1728
Gln Gly Gln Thr Arg Arg Tyr Gln Phe Ala Asn Tyr Arg Phe Thr Leu
            565                 570                 575 gtc gcc acc gtt acg att gac gaa ttg ccc aaa ggt acc tct ccc ctt    1776
Val Ala Thr Val Thr Ile Asp Glu Leu Pro Lys Gly Thr Ser Pro Leu
        580                 585                 590 ctt ggt gcc ggg tta gaa ggt cca ggc gac gct aaa ttg cta ggt tta    1824
Leu Gly Ala Gly Leu Glu Gly Pro Gly Asp Ala Lys Leu Leu Gly Leu
            595                 600                 605 tct tac gac aag aac cgt caa tgg cga ccc ttg tac gga gca gcc cct    1872
Ser Tyr Asp Lys Asn Arg Gln Trp Arg Pro Leu Tyr Gly Ala Ala Pro
610                 615                 620 gct tct cct aca gga tct tgg gag cta cac aag aag tac cat gta gtc    1920
Ala Ser Pro Thr Gly Ser Trp Glu Leu His Lys Lys Tyr His Val Val
625                 630                 635                 640 ctg acc atg gct gac aga cag ggg agt gtt tat gtt gat ggg caa cct    1968
Leu Thr Met Ala Asp Arg Gln Gly Ser Val Tyr Val Asp Gly Gln Pro
            645                 650                 655 ctt gcc gga tca ggc aat acc gtg gtt aga gga gct act ttg cca gac    2016
Leu Ala Gly Ser Gly Asn Thr Val Val Arg Gly Ala Thr Leu Pro Asp
        660                 665                 670 atc tct cac ttc tac att ggt gga ccc aga tct aag gga gcc cct aca    2064
Ile Ser His Phe Tyr Ile Gly Gly Pro Arg Ser Lys Gly Ala Pro Thr
            675                 680                 685 gat agt aga gtt aca gtg act aac gtg gtt tta tat aat cgt aga ctg    2112
Asp Ser Arg Val Thr Val Thr Asn Val Val Leu Tyr Asn Arg Arg Leu
        690                 695                 700 aac tct agt gag atc cgt aca ctt ttt ttg tct caa gac atg ata ggt    2160
Asn Ser Ser Glu Ile Arg Thr Leu Phe Leu Ser Gln Asp Met Ile Gly
705                 710                 715                 720 acc gat ggt gga gct ggt aca gca gca ttt cta gaa caa aaa ctc atc    2208
Thr Asp Gly Gly Ala Gly Thr Ala Ala Phe Leu Glu Gln Lys Leu Ile
            725                 730                 735 tca gaa gag gat ctg aat agc gcc gtc gac cat cat cat cat cat cat    2256
Ser Glu Glu Asp Leu Asn Ser Ala Val Asp His His His His His His
            740                 745                 750 tga                                                                 2259

<210> SEQ ID NO 12
<211> LENGTH: 91
<212> TYPE: PRT
<213> ORGANISM: Trypanosoma rangeli
```

```
<400> SEQUENCE: 12

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Ser
                85                  90

<210> SEQ ID NO 13
<211> LENGTH: 638
<212> TYPE: PRT
<213> ORGANISM: Trypanosoma rangeli

<400> SEQUENCE: 13

Leu Ala Pro Gly Ser Ser Arg Val Glu Leu Phe Lys Arg Lys Asn Ser
1               5                   10                  15

Thr Val Pro Phe Glu Glu Ser Asn Gly Thr Ile Arg Glu Arg Val Val
            20                  25                  30

His Ser Phe Arg Leu Pro Thr Ile Val Asn Val Asp Gly Val Met Val
        35                  40                  45

Ala Ile Ala Asp Ala Arg Tyr Glu Thr Ser Phe Asp Asn Ser Phe Ile
    50                  55                  60

Glu Thr Ala Val Lys Tyr Ser Val Asp Asp Gly Ala Thr Trp Asn Thr
65                  70                  75                  80

Gln Ile Ala Ile Lys Asn Ser Arg Ala Ser Ser Val Ser Arg Val Val
                85                  90                  95

Asp Pro Thr Val Ile Val Lys Gly Asn Lys Leu Tyr Ile Leu Val Gly
            100                 105                 110

Ser Phe Asn Lys Thr Arg Asn Tyr Trp Thr Gln His Arg Asp Gly Ser
        115                 120                 125

Asp Trp Glu Pro Leu Leu Val Val Gly Glu Val Thr Lys Ser Ala Ala
    130                 135                 140

Asn Gly Lys Thr Thr Ala Thr Ile Ser Trp Gly Lys Pro Val Ser Leu
145                 150                 155                 160

Lys Pro Leu Phe Pro Ala Glu Phe Asp Gly Ile Leu Thr Lys Glu Phe
                165                 170                 175

Val Gly Val Gly Ala Ala Ile Val Ala Ser Asn Gly Asn Leu Val
            180                 185                 190

Tyr Pro Val Gln Val Thr Asn Lys Lys Gln Val Phe Thr Lys Ile
        195                 200                 205

Met Tyr Ser Glu Asp Asp Gly Asn Thr Trp Lys Phe Ala Glu Gly Arg
    210                 215                 220

Ser Lys Phe Gly Cys Ser Glu Pro Ala Val Leu Glu Trp Gly Lys
225                 230                 235                 240

Leu Ile Ile Asn Asn Arg Val Asp Tyr Asn Arg Arg Leu Val Tyr Glu
                245                 250                 255

Ser Ser Asp Met Gly Lys Thr Val Glu Ala Leu Gly Thr Leu Ser
            260                 265                 270
```

-continued

```
His Val Trp Thr Asn Ser Pro Thr Ser Asn Gln Pro Asp Cys Gln Ser
            275                 280                 285

Ser Phe Val Ala Val Thr Ile Glu Gly Lys Arg Val Met Leu Phe Thr
290                 295                 300

His Pro Leu Asn Leu Lys Gly Arg Trp Met Arg Asp Arg Leu His Leu
305                 310                 315                 320

Trp Met Thr Asp Asn Gln Arg Ile Phe Asp Val Gly Gln Ile Ser Ile
                325                 330                 335

Gly Asp Glu Asn Ser Gly Tyr Ser Ser Val Leu Tyr Lys Asp Asp Lys
                340                 345                 350

Leu Tyr Ser Leu His Glu Ile Asn Thr Asn Asp Val Tyr Ser Leu Val
355                 360                 365

Phe Val Arg Leu Ile Gly Glu Leu Gln Leu Met Lys Ser Val Val Arg
370                 375                 380

Thr Trp Lys Glu Glu Asp Asn His Leu Ala Ser Ile Cys Thr Pro Val
385                 390                 395                 400

Val Pro Ala Thr Pro Ser Lys Gly Ala Cys Gly Ala Ala Val Pro
                405                 410                 415

Thr Ala Gly Leu Val Gly Phe Leu Ser His Ser Ala Asn Gly Ser Val
                420                 425                 430

Trp Glu Asp Val Tyr Arg Cys Val Asp Ala Asn Val Ala Asn Ala Glu
                435                 440                 445

Arg Val Pro Asn Gly Leu Lys Phe Asn Gly Val Gly Gly Ala Val
450                 455                 460

Trp Pro Val Ala Arg Gln Gly Gln Thr Arg Arg Tyr Gln Phe Ala Asn
465                 470                 475                 480

Tyr Arg Phe Thr Leu Val Ala Thr Val Thr Ile Asp Glu Leu Pro Lys
                485                 490                 495

Gly Thr Ser Pro Leu Leu Gly Ala Gly Leu Glu Gly Pro Gly Asp Ala
                500                 505                 510

Lys Leu Leu Gly Leu Ser Tyr Asp Lys Asn Arg Gln Trp Arg Pro Leu
                515                 520                 525

Tyr Gly Ala Ala Pro Ala Ser Pro Thr Gly Ser Trp Glu Leu His Lys
530                 535                 540

Lys Tyr His Val Val Leu Thr Met Ala Asp Arg Gln Gly Ser Val Tyr
545                 550                 555                 560

Val Asp Gly Gln Pro Leu Ala Gly Ser Gly Asn Thr Val Val Arg Gly
                565                 570                 575

Ala Thr Leu Pro Asp Ile Ser His Phe Tyr Ile Gly Gly Pro Arg Ser
                580                 585                 590

Lys Gly Ala Pro Thr Asp Ser Arg Val Thr Val Thr Asn Val Val Leu
                595                 600                 605

Tyr Asn Arg Arg Leu Asn Ser Ser Glu Ile Arg Thr Leu Phe Leu Ser
610                 615                 620

Gln Asp Met Ile Gly Thr Asp Gly Gly Ala Gly Thr Ala Ala
625                 630                 635

<210> SEQ ID NO 14
<211> LENGTH: 23
<212> TYPE: PRT
<213> ORGANISM: Trypanosoma rangeli

<400> SEQUENCE: 14

Phe Leu Glu Gln Lys Leu Ile Ser Glu Glu Asp Leu Asn Ser Ala Val
1               5                   10                  15
```

```
Asp His His His His His His
            20

<210> SEQ ID NO 15
<211> LENGTH: 25
<212> TYPE: DNA
<213> ORGANISM: Trypanosoma rangeli
<220> FEATURE:
<221> NAME/KEY: primer_bind
<222> LOCATION: (1)..(25)
<223> OTHER INFORMATION: Tr_fwd PCR primer - Tr6 trans-sialidase gene

<400> SEQUENCE: 15
gctctcgaga agagagaggc tgaag                                           25

<210> SEQ ID NO 16
<211> LENGTH: 26
<212> TYPE: DNA
<213> ORGANISM: Trypanosoma rangeli
<220> FEATURE:
<221> NAME/KEY: primer_bind
<222> LOCATION: (1)..(26)
<223> OTHER INFORMATION: Tr_rev PCR primer - Tr6 trans-sialidase gene

<400> SEQUENCE: 16
cgctctagaa atgctgctgt accagc                                          26

<210> SEQ ID NO 17
<211> LENGTH: 34
<212> TYPE: DNA
<213> ORGANISM: Trypanosoma rangeli
<220> FEATURE:
<221> NAME/KEY: primer_bind
<222> LOCATION: (1)..(34)
<223> OTHER INFORMATION: Q123S_F mutation primer for Tr6 gene

<400> SEQUENCE: 17
ctattggacc tctcacagag atggatctga ctgg                                 34

<210> SEQ ID NO 18
<211> LENGTH: 35
<212> TYPE: DNA
<213> ORGANISM: Trypanosoma rangeli
<220> FEATURE:
<221> NAME/KEY: primer_bind
<222> LOCATION: (1)..(35)
<223> OTHER INFORMATION: Q123S_R mutation primer for Tr6 gene

<400> SEQUENCE: 18
catctctgtg agaggtccaa tagttccttg tcttg                                35

<210> SEQ ID NO 19
<211> LENGTH: 33
<212> TYPE: DNA
<213> ORGANISM: Trypanosoma rangeli
<220> FEATURE:
<221> NAME/KEY: primer_bind
<222> LOCATION: (1)..(33)
<223> OTHER INFORMATION: R125G_F mutation primer for Tr6 gene

<400> SEQUENCE: 19
gacccagcac ggagatggat ctgactggga acc                                  33

<210> SEQ ID NO 20
<211> LENGTH: 33
<212> TYPE: DNA
<213> ORGANISM: Trypanosoma rangeli
```

-continued

<220> FEATURE:
<221> NAME/KEY: primer_bind
<222> LOCATION: (1)..(33)
<223> OTHER INFORMATION: R125G_R mutation primer for Tr6 gene

<400> SEQUENCE: 20
cagatccatc tccgtgctgg gtccaatagt tcc 33

<210> SEQ ID NO 21
<211> LENGTH: 34
<212> TYPE: DNA
<213> ORGANISM: Trypanosoma rangeli
<220> FEATURE:
<221> NAME/KEY: primer_bind
<222> LOCATION: (1)..(34)
<223> OTHER INFORMATION: G127A_F mutation primer for Tr6 gene

<400> SEQUENCE: 21
gcacagagat gcttctgact gggaaccatt gttg 34

<210> SEQ ID NO 22
<211> LENGTH: 35
<212> TYPE: DNA
<213> ORGANISM: Trypanosoma rangeli
<220> FEATURE:
<221> NAME/KEY: primer_bind
<222> LOCATION: (1)..(35)
<223> OTHER INFORMATION: G127A_R mutation primer for Tr6 gene

<400> SEQUENCE: 22
cccagtcaga agcatctctg tgctgggtcc aatag 35

<210> SEQ ID NO 23
<211> LENGTH: 32
<212> TYPE: DNA
<213> ORGANISM: Trypanosoma rangeli
<220> FEATURE:
<221> NAME/KEY: primer_bind
<222> LOCATION: (1)..(32)
<223> OTHER INFORMATION: E175Q_F mutation primer for Tr6 gene

<400> SEQUENCE: 23
acttactaag cagttcgtag gtggagtagg cg 32

<210> SEQ ID NO 24
<211> LENGTH: 40
<212> TYPE: DNA
<213> ORGANISM: Trypanosoma rangeli
<220> FEATURE:
<221> NAME/KEY: primer_bind
<222> LOCATION: (1)..(40)
<223> OTHER INFORMATION: E175Q_R mutation primer for Tr6 gene

<400> SEQUENCE: 24
ctccacctac gaactgctta gtaagtatgc cgtcgaactc 40

<210> SEQ ID NO 25
<211> LENGTH: 29
<212> TYPE: DNA
<213> ORGANISM: Trypanosoma rangeli
<220> FEATURE:
<221> NAME/KEY: primer_bind
<222> LOCATION: (1)..(29)
<223> OTHER INFORMATION: V177L_F mutation primer for Tr6 gene

<400> SEQUENCE: 25
taaggaattc ttgggtggag taggcgccg 29

<210> SEQ ID NO 26
<211> LENGTH: 39
<212> TYPE: DNA
<213> ORGANISM: Trypanosoma rangeli
<220> FEATURE:
<221> NAME/KEY: primer_bind
<222> LOCATION: (1)..(39)
<223> OTHER INFORMATION: V177L_R mutation primer for Tr6 gene

<400> SEQUENCE: 26
cctactccac ccaagaattc cttagtaagt atgccgtcg                       39

<210> SEQ ID NO 27
<211> LENGTH: 28
<212> TYPE: DNA
<213> ORGANISM: Trypanosoma rangeli
<220> FEATURE:
<221> NAME/KEY: primer_bind
<222> LOCATION: (1)..(28)
<223> OTHER INFORMATION: V180A_F mutation primer for Tr6 gene

<400> SEQUENCE: 27
cgtaggtgga gctggcgccg ccatcgtg                                   28

<210> SEQ ID NO 28
<211> LENGTH: 37
<212> TYPE: DNA
<213> ORGANISM: Trypanosoma rangeli
<220> FEATURE:
<221> NAME/KEY: primer_bind
<222> LOCATION: (1)..(37)
<223> OTHER INFORMATION: V180A_R mutation primer for Tr6 gene

<400> SEQUENCE: 28
tggcggcgcc agctccacct acgaattcct tagtaag                         37

<210> SEQ ID NO 29
<211> LENGTH: 43
<212> TYPE: DNA
<213> ORGANISM: Trypanosoma rangeli
<220> FEATURE:
<221> NAME/KEY: primer_bind
<222> LOCATION: (1)..(43)
<223> OTHER INFORMATION: G202K_F mutation primer for Tr6 gene

<400> SEQUENCE: 29
tgctgacatg aagggaagag tatttacaaa aattatgtat tcc                  43

<210> SEQ ID NO 30
<211> LENGTH: 33
<212> TYPE: DNA
<213> ORGANISM: Trypanosoma rangeli
<220> FEATURE:
<221> NAME/KEY: primer_bind
<222> LOCATION: (1)..(33)
<223> OTHER INFORMATION: G202K_R mutation primer for Tr6 gene

<400> SEQUENCE: 30
atactcttcc cttcatgtca gcaatttgca cag                             33

<210> SEQ ID NO 31
<211> LENGTH: 34
<212> TYPE: DNA
<213> ORGANISM: Trypanosoma rangeli
<220> FEATURE:
<221> NAME/KEY: primer_bind
<222> LOCATION: (1)..(34)
<223> OTHER INFORMATION: N250R_F mutation primer for Tr6 gene

<400> SEQUENCE: 31
agtcgattac agaagacgtc tggtgtacga atcc                                34

<210> SEQ ID NO 32
<211> LENGTH: 41
<212> TYPE: DNA
<213> ORGANISM: Trypanosoma rangeli
<220> FEATURE:
<221> NAME/KEY: primer_bind
<222> LOCATION: (1)..(41)
<223> OTHER INFORMATION: N250R_R mutation primer for Tr6 gene

<400> SEQUENCE: 32
ccagacgtct tctgtaatcg actcggttat taatgattag c                        41

<210> SEQ ID NO 33
<211> LENGTH: 41
<212> TYPE: DNA
<213> ORGANISM: Trypanosoma rangeli
<220> FEATURE:
<221> NAME/KEY: primer_bind
<222> LOCATION: (1)..(41)
<223> OTHER INFORMATION: D363E_F mutation primer for Tr6 gene

<400> SEQUENCE: 33
gagattaata ctaatgaggt ttattctctt gttttttgtcc g                       41

<210> SEQ ID NO 34
<211> LENGTH: 52
<212> TYPE: DNA
<213> ORGANISM: Trypanosoma rangeli
<220> FEATURE:
<221> NAME/KEY: primer_bind
<222> LOCATION: (1)..(52)
<223> OTHER INFORMATION: D363E_R mutation primer for Tr6 gene

<400> SEQUENCE: 34
caagagaata aacctcatta gtattaatct catgtaggga atataattta tc            52

<210> SEQ ID NO 35
<211> LENGTH: 59
<212> TYPE: DNA
<213> ORGANISM: Trypanosoma rangeli
<220> FEATURE:
<221> NAME/KEY: primer_bind
<222> LOCATION: (1)..(59)
<223> OTHER INFORMATION: VTNKKKQ 197-203 _F mutation primer for Tr6 gene

<400> SEQUENCE: 35
ccctgtgcaa gtaactaata agaagaagca agtatttaca aaaattatgt attccgagg     59

<210> SEQ ID NO 36
<211> LENGTH: 54
<212> TYPE: DNA
<213> ORGANISM: Trypanosoma rangeli
<220> FEATURE:
<221> NAME/KEY: primer_bind
<222> LOCATION: (1)..(54)
<223> OTHER INFORMATION: VTNKKKQ 197-203 _R mutation primer for Tr6 gene

<400> SEQUENCE: 36
ttgtaaatac ttgcttcttc ttattagtta cttgcacagg gtataccaaa ttac          54

<210> SEQ ID NO 37
<211> LENGTH: 40
<212> TYPE: DNA

```
<213> ORGANISM: Trypanosoma rangeli
<220> FEATURE:
<221> NAME/KEY: primer_bind
<222> LOCATION: (1)..(40)
<223> OTHER INFORMATION: P98A_F mutation primer for Tr6 gene

<400> SEQUENCE: 37
ggttgtcgat gctacggtca tagtaaaggg aaataagttg                     40

<210> SEQ ID NO 38
<211> LENGTH: 33
<212> TYPE: DNA
<213> ORGANISM: Trypanosoma rangeli
<220> FEATURE:
<221> NAME/KEY: primer_bind
<222> LOCATION: (1)..(33)
<223> OTHER INFORMATION: P98A_R mutation primer for Tr6 gene

<400> SEQUENCE: 38
ctatgaccgt agcatcgaca acccttgaaa ctg                            33

<210> SEQ ID NO 39
<211> LENGTH: 36
<212> TYPE: DNA
<213> ORGANISM: Trypanosoma rangeli
<220> FEATURE:
<221> NAME/KEY: primer_bind
<222> LOCATION: (1)..(36)
<223> OTHER INFORMATION: Y249G_F mutation primer for Tr6 gene

<400> SEQUENCE: 39
ccgagtcgat ggaaatagac gtctggtgta cgaatc                         36

<210> SEQ ID NO 40
<211> LENGTH: 38
<212> TYPE: DNA
<213> ORGANISM: Trypanosoma rangeli
<220> FEATURE:
<221> NAME/KEY: primer_bind
<222> LOCATION: (1)..(38)
<223> OTHER INFORMATION: Y249G_R mutation primer for Tr6 gene

<400> SEQUENCE: 40
gacgtctatt tccatcgact cggttattaa tgattagc                       38

<210> SEQ ID NO 41
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant motif where Xaa is K or R

<400> SEQUENCE: 41

Ile Ala Xaa Met Gly Gly Arg
1               5

<210> SEQ ID NO 42
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant motif
<220> FEATURE:
<221> NAME/KEY: DOMAIN
<222> LOCATION: (2)..(2)
```

```
<223> OTHER INFORMATION: Xaa is K or R
<220> FEATURE:
<221> NAME/KEY: DOMAIN
<222> LOCATION: (3)..(3)
<223> OTHER INFORMATION: Xaa is a neutral amino acid

<400> SEQUENCE: 42

Ile Xaa Xaa Met Gly Gly Arg
1               5

<210> SEQ ID NO 43
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant motif
<220> FEATURE:
<221> NAME/KEY: DOMAIN
<222> LOCATION: (3)..(3)
<223> OTHER INFORMATION: Xaa is a neutral amino acid
<220> FEATURE:
<221> NAME/KEY: DOMAIN
<222> LOCATION: (4)..(4)
<223> OTHER INFORMATION: where Xaa is K or R

<400> SEQUENCE: 43

Ile Ala Xaa Xaa Gly Gly Arg
1               5

<210> SEQ ID NO 44
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant motif
<220> FEATURE:
<221> NAME/KEY: DOMAIN
<222> LOCATION: (3)..(3)
<223> OTHER INFORMATION: Xaa is a neutral amino acid
<220> FEATURE:
<221> NAME/KEY: DOMAIN
<222> LOCATION: (5)..(5)
<223> OTHER INFORMATION: Xaa is K or R

<400> SEQUENCE: 44

Ile Ala Xaa Met Xaa Gly Arg
1               5

<210> SEQ ID NO 45
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant motif
<220> FEATURE:
<221> NAME/KEY: DOMAIN
<222> LOCATION: (3)..(3)
<223> OTHER INFORMATION: Xaa is a neutral amino acid
<220> FEATURE:
<221> NAME/KEY: DOMAIN
<222> LOCATION: (6)..(6)
<223> OTHER INFORMATION: where Xaa is K or R

<400> SEQUENCE: 45

Ile Ala Xaa Met Gly Xaa Arg
1               5
```

```
<210> SEQ ID NO 46
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant motif where Xaa is K or R

<400> SEQUENCE: 46

Ile Xaa Asp Xaa Gly Gly Arg
1               5

<210> SEQ ID NO 47
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant motif where where Xaa is K or R

<400> SEQUENCE: 47

Ile Xaa Asp Met Xaa Gly Arg
1               5

<210> SEQ ID NO 48
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant motif where where Xaa is K or R

<400> SEQUENCE: 48

Ile Xaa Asp Met Gly Xaa Arg
1               5

<210> SEQ ID NO 49
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant motif where Xaa is K or R

<400> SEQUENCE: 49

Ile Ala Asp Xaa Xaa Gly Arg
1               5

<210> SEQ ID NO 50
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant motif where Xaa is K or R

<400> SEQUENCE: 50

Ile Ala Asp Met Xaa Xaa Arg
1               5

<210> SEQ ID NO 51
<211> LENGTH: 7
```

```
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant motif
<220> FEATURE:
<221> NAME/KEY: DOMAIN
<222> LOCATION: (2)..(2)
<223> OTHER INFORMATION: Xaa is K or R
<220> FEATURE:
<221> NAME/KEY: DOMAIN
<222> LOCATION: (3)..(3)
<223> OTHER INFORMATION: where Xaa is a neutral amino acid
<220> FEATURE:
<221> NAME/KEY: DOMAIN
<222> LOCATION: (4)..(4)
<223> OTHER INFORMATION: where Xaa is K or R

<400> SEQUENCE: 51

Ile Xaa Xaa Xaa Gly Gly Arg
1               5

<210> SEQ ID NO 52
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant motif
<220> FEATURE:
<221> NAME/KEY: DOMAIN
<222> LOCATION: (3)..(3)
<223> OTHER INFORMATION: where Xaa is a neutral amino acid
<220> FEATURE:
<221> NAME/KEY: DOMAIN
<222> LOCATION: (4)..(5)
<223> OTHER INFORMATION: where Xaa is K or R

<400> SEQUENCE: 52

Ile Ala Xaa Xaa Xaa Gly Arg
1               5

<210> SEQ ID NO 53
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant motif
<220> FEATURE:
<221> NAME/KEY: DOMAIN
<222> LOCATION: (3)..(3)
<223> OTHER INFORMATION: where Xaa is a neutral amino acid
<220> FEATURE:
<221> NAME/KEY: DOMAIN
<222> LOCATION: (5)..(6)
<223> OTHER INFORMATION: where Xaa is K or R

<400> SEQUENCE: 53

Ile Ala Xaa Met Xaa Xaa Arg
1               5

<210> SEQ ID NO 54
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant motif where Xaa is K or R
```

```
<400> SEQUENCE: 54

Ile Ala Xaa Met Gly Xaa Arg
1               5

<210> SEQ ID NO 55
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant motif wherein Xaa is K or R and

<400> SEQUENCE: 55

Ile Ala Xaa Met Xaa Gly Arg
1               5

<210> SEQ ID NO 56
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant motif where Xaa is K or R

<400> SEQUENCE: 56

Ile Ala Xaa Xaa Gly Gly Arg
1               5

<210> SEQ ID NO 57
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant motif
<220> FEATURE:
<221> NAME/KEY: DOMAIN
<222> LOCATION: (3)..(3)
<223> OTHER INFORMATION: wherein Xaa is a neutral amino acid
<220> FEATURE:
<221> NAME/KEY: DOMAIN
<222> LOCATION: (4)..(6)
<223> OTHER INFORMATION: wherein Xaa is a K or R
<220> FEATURE:
<221> NAME/KEY: DOMAIN
<222> LOCATION: (7)..(7)
<223> OTHER INFORMATION: wherein Xaa is a neutral amino acid

<400> SEQUENCE: 57

Ile Ala Xaa Xaa Xaa Xaa Xaa
1               5

<210> SEQ ID NO 58
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant domain

<400> SEQUENCE: 58

Val Thr Asn Lys Lys Lys Gln
1               5
```

```
<210> SEQ ID NO 59
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant domain

<400> SEQUENCE: 59

Ala Arg Asn Lys Ala Asn Arg
1               5

<210> SEQ ID NO 60
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant domain

<400> SEQUENCE: 60

Ile Ala Asn Lys Lys Lys Gln
1               5

<210> SEQ ID NO 61
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant motif

<400> SEQUENCE: 61

Ile Ala Asn Arg Arg Arg Gln
1               5

<210> SEQ ID NO 62
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant motif

<400> SEQUENCE: 62

Ile Ala Asp Met Gly Gly Arg
1               5

<210> SEQ ID NO 63
<211> LENGTH: 7
<212> TYPE: PRT
<213> ORGANISM: Trypanosoma cruzi
<220> FEATURE:
<221> NAME/KEY: DOMAIN
<222> LOCATION: (1)..(7)
<223> OTHER INFORMATION: Mutant motif

<400> SEQUENCE: 63

Ile Ala Asp Met Lys Gly Arg
1               5
```